United States Patent
Kerns et al.

(10) Patent No.: US 8,568,391 B2
(45) Date of Patent: Oct. 29, 2013

(54) STERILE SURGICAL TRAY

(75) Inventors: Ralph Kerns, Laguna Niguel, CA (US); Mark Humayun, Glendale, CA (US); Matthew T. McCormick, Yucaipa, CA (US); Trent Spencer Wells, Altadena, CA (US); Lawrence Chong, Seal Beach, CA (US); Jaw Chyng Lue, Alhambra, CA (US)

(73) Assignee: Doheny Eye Institute, Los Angeles, CA (US)

( * ) Notice: Subject to any disclaimer, the term of this patent is extended or adjusted under 35 U.S.C. 154(b) by 27 days.

(21) Appl. No.: 13/312,948

(22) Filed: Dec. 6, 2011

(65) Prior Publication Data

US 2012/0325704 A1    Dec. 27, 2012

Related U.S. Application Data

(63) Continuation-in-part of application No. 12/684,850, filed on Jan. 8, 2010, which is a continuation-in-part of application No. 12/256,420, filed on Oct. 22, 2008, which is a continuation-in-part of application No. 12/107,038, filed on Apr. 21, 2008, said application No. 12/256,420 is a continuation-in-part of application No. 12/106,962, filed on Apr. 21, 2008.

(60) Provisional application No. 60/925,546, filed on Apr. 20, 2007, provisional application No. 60/925,548, filed on Apr. 20, 2007, provisional application No. 61/481,637, filed on May 2, 2011.

(51) Int. Cl.
*A61B 17/00* (2006.01)
*A61B 9/00* (2006.01)
*A61B 17/32* (2006.01)

(52) U.S. Cl.
USPC ............... 606/1; 606/107; 606/167; 235/435; 235/441

(58) Field of Classification Search
USPC .......... 206/210, 363, 370, 564, 572; 235/435, 235/441, 451; 340/572.1; 433/77, 79, 433/98–101; 604/22; 606/1, 107, 167, 171, 606/174; 623/6.12, 905
See application file for complete search history.

(56) References Cited

U.S. PATENT DOCUMENTS 3,116,828 A    1/1964   Glassman
3,293,430 A   12/1966   Wustner
(Continued)

FOREIGN PATENT DOCUMENTS

EP     1 813 199 A1   8/2007
JP     2002-515293    5/2002
(Continued)

OTHER PUBLICATIONS

International Search Report and Written Opinion issued on Oct. 18, 2012 for International Application No. PCT/US2012/034480.

(Continued)

*Primary Examiner* — Ryan Severson
*Assistant Examiner* — Ashley Fishback
(74) *Attorney, Agent, or Firm* — Knobbe, Martens, Olson & Bear, LLP

(57) ABSTRACT

A surgical apparatus for use by a surgeon can include a tray and a plurality of surgical instruments. The tray can have a plurality of structures located on an upper side of the tray for receiving the plurality of surgical instruments. The tray can receive a separate control unit. The tray can also have a fluid reservoir receiver for receiving a bottle or container of fluid, such as balanced salt solution. The fluid reservoir receiver can include one or more features, including, a spike, an air vent, and a light. A separate container can be used to place the bottle or container of fluid into the fluid reservoir receiver on the tray. This separate container can include a collapsible section.

9 Claims, 27 Drawing Sheets

(56) References Cited

U.S. PATENT DOCUMENTS

| | | | |
|---|---|---|---|
| 3,304,609 A | | 2/1967 | Horowitz et al. |
| 3,366,230 A | | 1/1968 | Loran |
| 3,702,940 A | * | 11/1972 | Stewart .................... 307/326 |
| 3,820,656 A | | 6/1974 | Orr |
| 3,976,195 A | | 8/1976 | Cohen |
| 3,986,263 A | | 10/1976 | Borgelt et al. |
| 4,011,944 A | | 3/1977 | Cooley et al. |
| 4,014,342 A | | 3/1977 | Staub et al. |
| 4,108,182 A | | 8/1978 | Hartman et al. |
| 4,112,947 A | | 9/1978 | Nehring |
| 4,266,669 A | | 5/1981 | Watson |
| 4,288,733 A | | 9/1981 | Bilanceri et al. |
| 4,293,074 A | | 10/1981 | Dunsky |
| 4,320,761 A | | 3/1982 | Haddad |
| 4,378,108 A | | 3/1983 | Bailey, Jr. |
| 4,428,748 A | | 1/1984 | Peyman et al. |
| 4,430,062 A | | 2/1984 | Henrichsen et al. |
| 4,479,762 A | | 10/1984 | Bilstad et al. |
| 4,735,610 A | | 4/1988 | Akkas et al. |
| 4,798,580 A | | 1/1989 | DeMeo et al. |
| 4,869,266 A | | 9/1989 | Taylor et al. |
| 4,889,231 A | | 12/1989 | Foote et al. |
| 4,930,997 A | | 6/1990 | Bennett |
| 4,974,728 A | | 12/1990 | Colton |
| 5,013,240 A | | 5/1991 | Bailey et al. |
| 5,078,677 A | | 1/1992 | Gentelia et al. |
| 5,392,917 A | | 2/1995 | Alpern et al. |
| 5,399,007 A | | 3/1995 | Marconet |
| 5,455,766 A | | 10/1995 | Scheller et al. |
| 5,508,836 A | | 4/1996 | DeCaro et al. |
| 5,586,163 A | | 12/1996 | Goldstein |
| 5,627,584 A | | 5/1997 | Nishikori et al. |
| 5,746,719 A | | 5/1998 | Farra et al. |
| 5,779,053 A | | 7/1998 | Partika et al. |
| 5,873,717 A | | 2/1999 | Behringer |
| 5,910,110 A | | 6/1999 | Bastable |
| 6,022,088 A | | 2/2000 | Metzler |
| 6,024,699 A | | 2/2000 | Surwit et al. |
| 6,051,011 A | | 4/2000 | Weidenbenner |
| 6,059,795 A | | 5/2000 | Wallace et al. |
| 6,074,399 A | | 6/2000 | Wallace et al. |
| 6,117,127 A | | 9/2000 | Helmreich et al. |
| 6,158,437 A | | 12/2000 | Vagley |
| 6,185,096 B1 | | 2/2001 | Helot et al. |
| 6,217,584 B1 | | 4/2001 | Nun |
| 6,251,113 B1 | | 6/2001 | Appelbaum et al. |
| 6,258,111 B1 | | 7/2001 | Ross et al. |
| 6,312,258 B1 | | 11/2001 | Ashman |
| 6,355,047 B1 | | 3/2002 | Wallace et al. |
| 6,428,487 B1 | | 8/2002 | Burdorff |
| 6,616,606 B1 | | 9/2003 | Petersen et al. |
| 6,641,039 B2 | | 11/2003 | Southard |
| 6,648,223 B2 | | 11/2003 | Boukhny et al. |
| 6,666,875 B1 | | 12/2003 | Sakurai et al. |
| 6,716,219 B1 | | 4/2004 | Koch |
| 6,896,141 B2 | | 5/2005 | McMichael et al. |
| 7,100,771 B2 | | 9/2006 | Massengale et al. |
| 7,114,500 B2 | | 10/2006 | Bonutti |
| 7,165,555 B2 | | 1/2007 | Lee |
| 7,267,246 B2 | | 9/2007 | Eiskant et al. |
| 7,331,463 B2 | | 2/2008 | Hickey |
| 7,362,228 B2 | | 4/2008 | Nycz et al. |
| 7,401,703 B2 | | 7/2008 | McMichael et al. |
| 7,431,157 B2 | | 10/2008 | Porret et al. |
| 7,604,007 B1 | | 10/2009 | Wooley |
| 2001/0022615 A1 | | 9/2001 | Fernandez et al. |
| 2002/0013517 A1 | | 1/2002 | West et al. |
| 2003/0093503 A1 | | 5/2003 | Yamaki et al. |
| 2003/0165794 A1 | * | 9/2003 | Matoba ...................... 433/114 |
| 2004/0004019 A1 | | 1/2004 | Busch |
| 2004/0116952 A1 | | 6/2004 | Sakurai et al. |
| 2004/0138518 A1 | | 7/2004 | Rise et al. |
| 2004/0139048 A1 | | 7/2004 | Kerr, II et al. |
| 2004/0186683 A1 | | 9/2004 | Farber et al. |
| 2004/0208780 A1 | | 10/2004 | Faries, Jr. et al. |
| 2004/0243147 A1 | | 12/2004 | Lipow |
| 2005/0128987 A1 | | 6/2005 | Liang |
| 2005/0245888 A1 | | 11/2005 | Cull |
| 2005/0283138 A1 | | 12/2005 | Tashiro et al. |
| 2006/0002258 A1 | | 1/2006 | Nakamura et al. |
| 2006/0046226 A1 | | 3/2006 | Bergler et al. |
| 2006/0086634 A1 | | 4/2006 | Steppe |
| 2006/0095066 A1 | | 5/2006 | Chang et al. |
| 2006/0100497 A1 | | 5/2006 | Sawazaki et al. |
| 2006/0109105 A1 | | 5/2006 | Varner et al. |
| 2006/0119481 A1 | | 6/2006 | Tethrake et al. |
| 2006/0142739 A1 | | 6/2006 | DiSilestro et al. |
| 2006/0244593 A1 | | 11/2006 | Nycz et al. |
| 2006/0255938 A1 | | 11/2006 | Van den Brink |
| 2006/0272979 A1 | | 12/2006 | Lubbers et al. |
| 2006/0289016 A1 | | 12/2006 | Kammer et al. |
| 2007/0290654 A1 | | 12/2007 | Govari et al. |
| 2008/0030345 A1 | | 2/2008 | Austin et al. |
| 2008/0041282 A1 | | 2/2008 | Goschy et al. |
| 2008/0120137 A1 | | 5/2008 | Nyholm |
| 2008/0272023 A1 | | 11/2008 | McCormick et al. |
| 2008/0281254 A1 | | 11/2008 | Humayun et al. |
| 2008/0281301 A1 | | 11/2008 | DeBoer et al. |
| 2009/0143734 A1 | | 6/2009 | Humayun et al. |
| 2010/0174415 A1 | | 7/2010 | Humayun et al. |
| 2011/0190690 A1 | | 8/2011 | Humayun et al. |
| 2011/0276340 A1 | | 11/2011 | DeBoer et al. |

FOREIGN PATENT DOCUMENTS

| | | |
|---|---|---|
| JP | 3088841 | 10/2002 |
| JP | 2005-046412 | 2/2005 |
| JP | 2006-511285 A | 4/2006 |
| WO | WO 99/59510 A1 | 11/1999 |
| WO | WO 99/66444 | 12/1999 |
| WO | WO 00/32115 | 6/2000 |
| WO | WO00/32123 | 6/2000 |
| WO | WO 03/034213 A2 | 4/2003 |
| WO | WO 2004/060184 A1 | 7/2004 |

OTHER PUBLICATIONS

U.S. Appl. No. 13/084,478, filed Apr. 11, 2011, including its prosecution history, the reference cited therein, and the Office Actions therein, Nov. 10, 2011, DeBoer, et al.
Extended European Search Report received in European Application No. 08746468.1, dated Nov. 23, 2010.
International Preliminary Report on Patentability and Written Opinion dated Apr. 26, 2011 in PCT Application No. PCT/US2008/080832, filed on Oct. 22, 2008.
International Preliminary Report on Patentability and Written Opinion dated Oct. 20, 2009 in PCT Application No. PCT/US2008/061058, filed on Apr. 21, 2008.
International Search Report and Written Opinion dated Aug. 27, 2008 for PCT Application PCT/US2008/061058, filed Apr. 21, 2008.
International Search Report and Written Opinion dated Dec. 22, 2008 in PCT Application No. PCT/US08/061065.
International Search Report and Written Opinion dated Jul. 29, 2010 in PCT Application No. PCT/US2008/080832, filed Oct. 22, 2008.
International Search Report and Written Opinion dated Jun. 2, 2011 in PCT Application No. PCT/US2011/020415 filed Jan. 6, 2011.
International Search Report and Written Opinion dated Sep. 2, 2008 in PCT Application No. PCT/US2008/061043, filed Apr. 21, 2008.
Partial International Search Report in Application No. PCT/US2008/080832 dated Apr. 27, 2010.
Merriam-Webster.com definition of "tray"; http://www.merriam-webster.com/dictionary/tray.
Partial International Search Report issued on Jul. 6, 2012 for International Application No. PCT/US2012/034480.

* cited by examiner

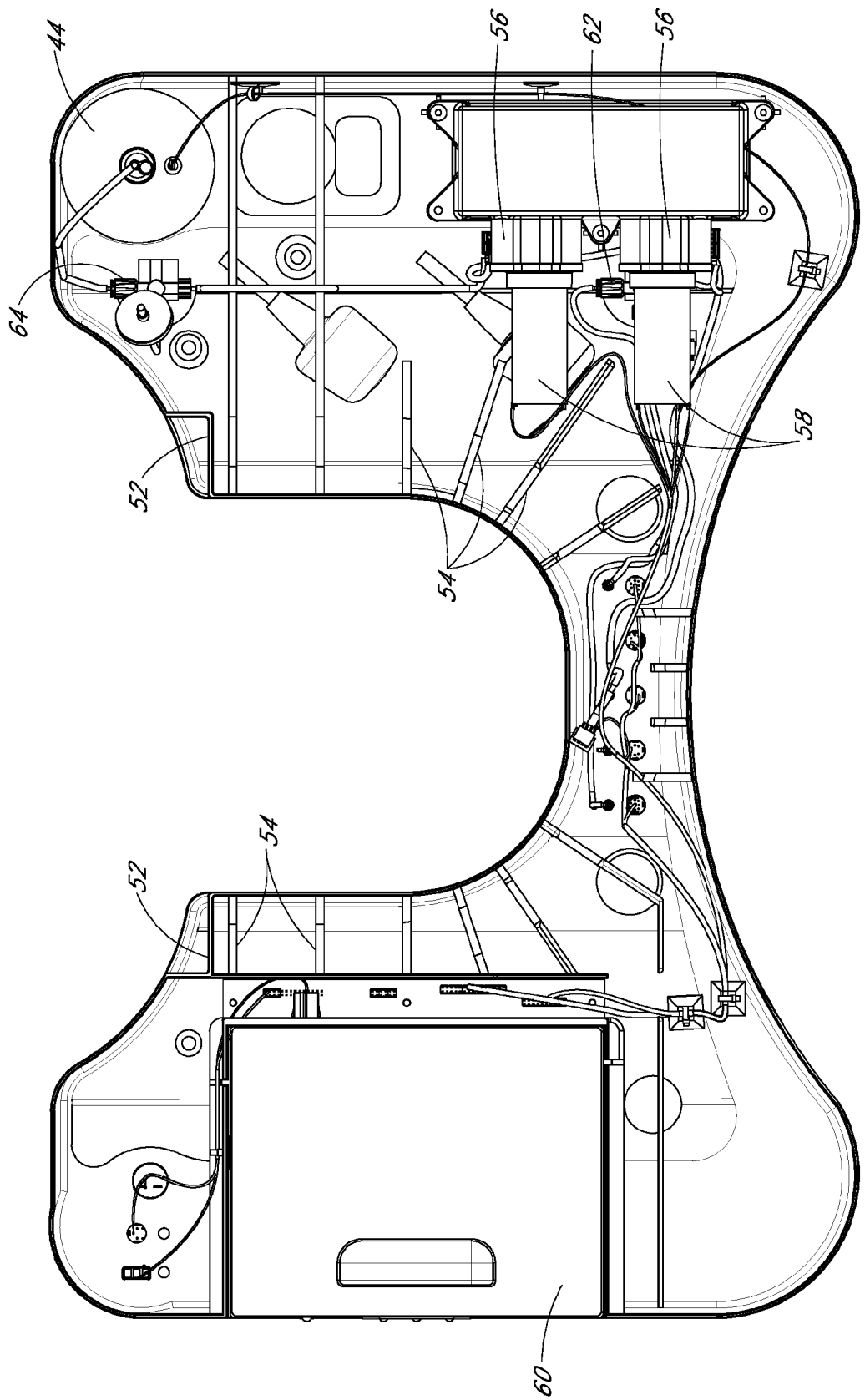

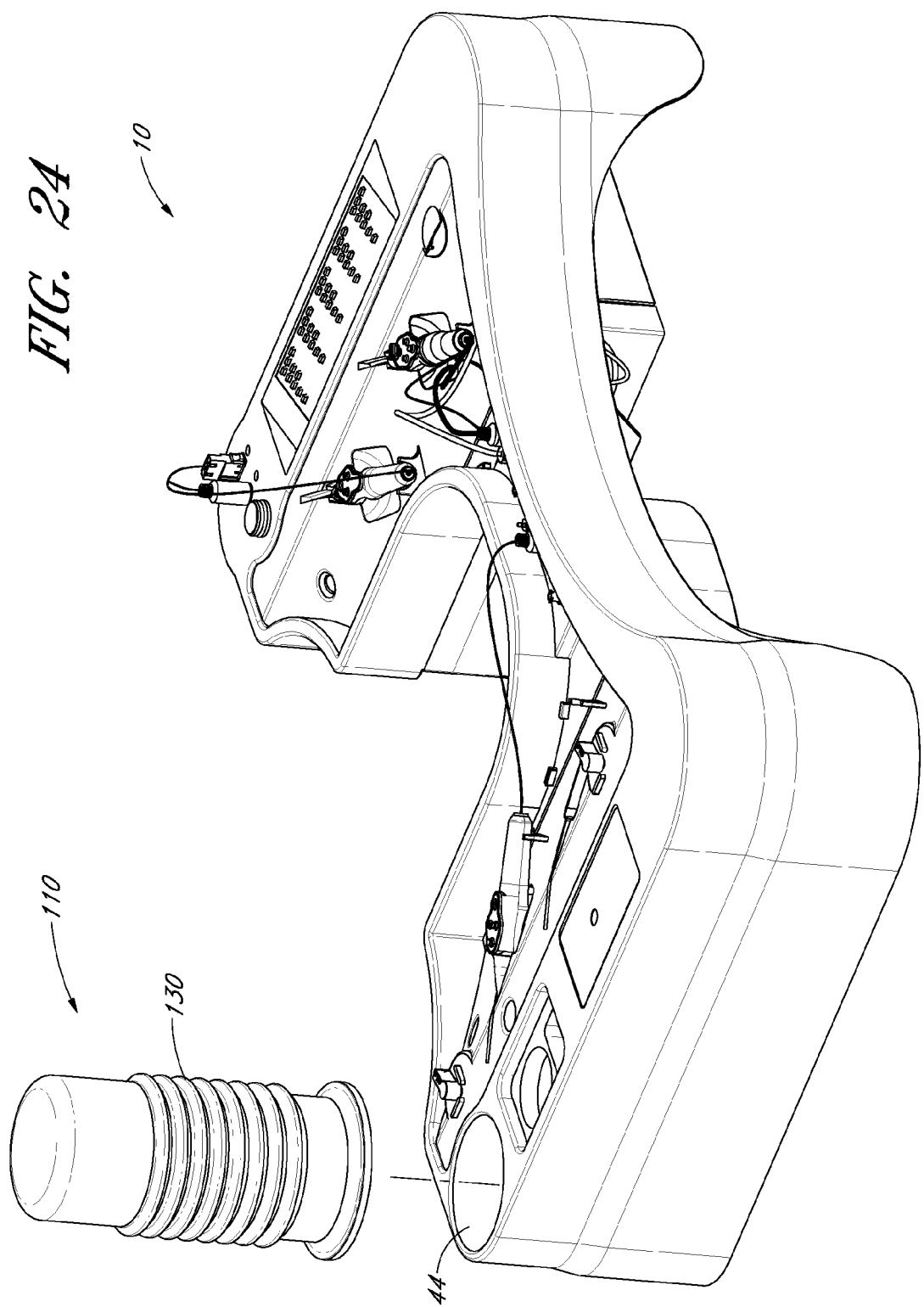

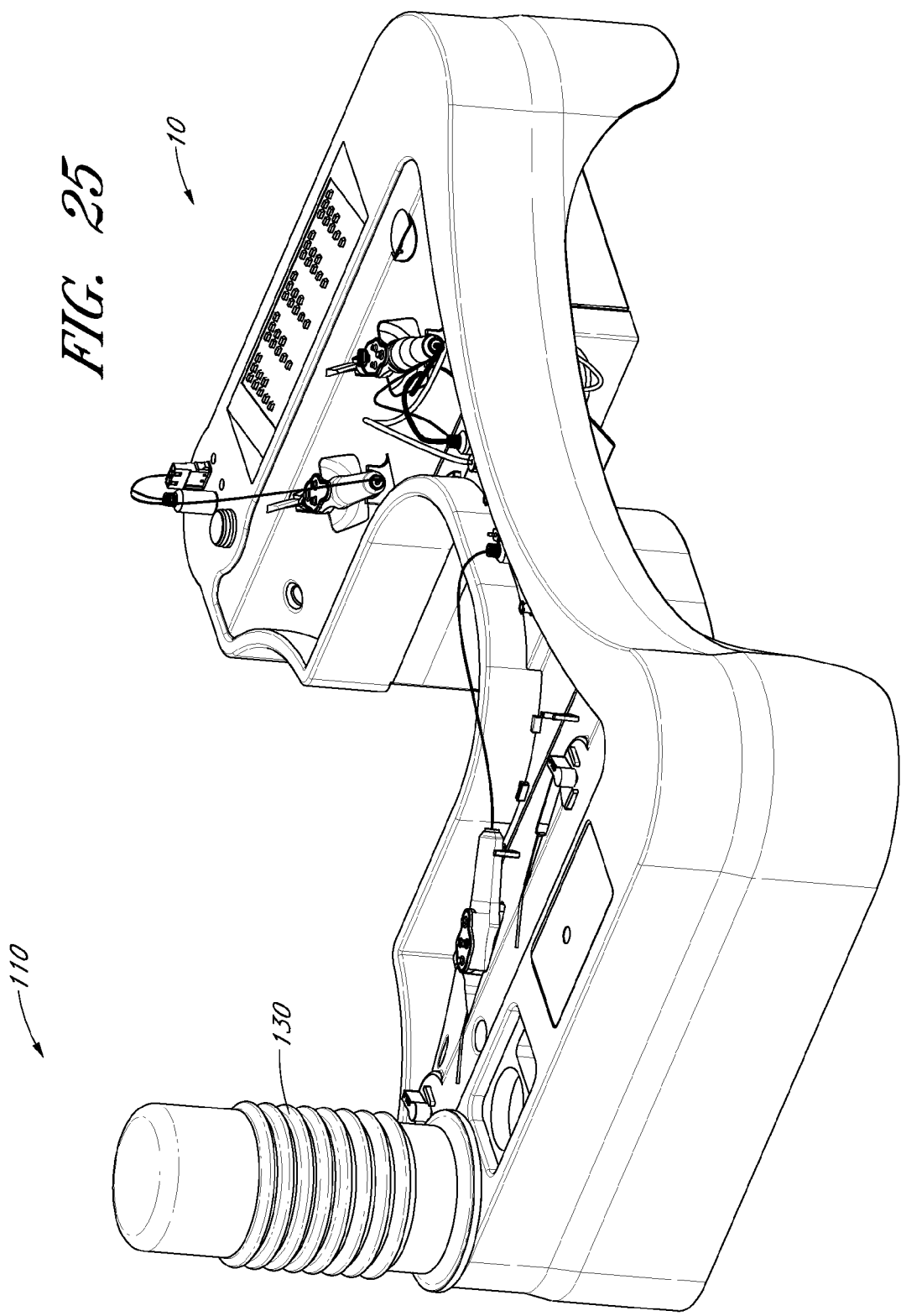

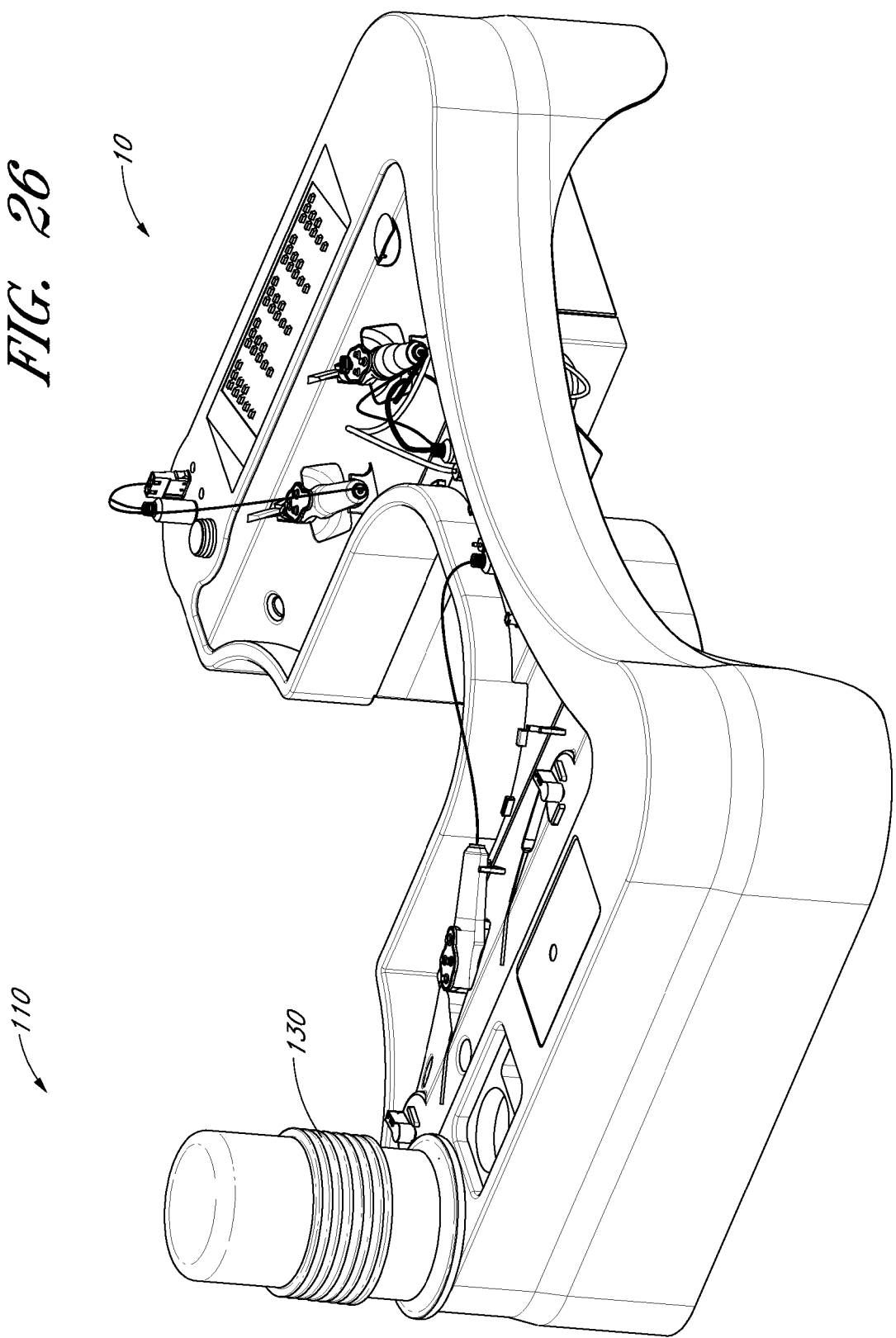

STERILE SURGICAL TRAY

CROSS-REFERENCE TO RELATED APPLICATIONS

This application is a continuation-in-part application of U.S. application Ser. No. 12/684,850 (DOHENY2.009CPCP1), filed Jan. 8, 2010, which is a continuation-in-part application of U.S. application Ser. No. 12/256,420 (DOHENY2.009CP1), filed Oct. 22, 2008, which is a continuation-in-part application of U.S. application Ser. No. 12/107,038 (DOHENY2.009A), filed Apr. 21, 2008, which claims the benefit of U.S. Provisional Application No. 60/925,546 filed Apr. 20, 2007. U.S. application Ser. No. 12/256,420 is also a continuation-in-part application of U.S. application Ser. No. 12/106,962 (DOHENY2.011A), filed Apr. 21, 2008, which claims the benefit of U.S. Provisional Application No. 60/925,548 filed Apr. 20, 2007. This application also claims the benefit of U.S. Provisional Application No. 61/481,637 (DOHENY2.059PR) filed May 2, 2011, titled STERILE BOTTLE CONTAINER AND METHOD. Each of the foregoing applications is hereby incorporated by reference herein in its entirety and should be considered a part of this application.

BACKGROUND

1. Field

The present invention relates generally to surgical systems and more particularly to sterile surgical trays that can be used with a plurality of surgical instruments in surgical procedures.

2. Description of the Related Art

It is well known to use, in surgery, a sterile pack shipped from a manufacturer to a surgery center, an example of which is ophthalmic surgery (vitreoretinal or cataract surgery, in particular). These packs typically contain several items that are used in surgery and may include one-time use surgical instruments, fluid cassettes, tubing sets, drapes, needles, and other devices. The particular content of a pack depends on the type of surgery and perhaps the individual preference of the surgeon or surgery center.

When preparing for surgery, typically a sterile drape is placed over what is commonly referred to as a Mayo tray. The contents of the sterile pack and perhaps additional sterile instruments and materials are spread-out over the tray so that the materials and instruments necessary for the surgery are readily available to a nurse or surgeon.

It is also known to provide a sterile pack where many of the instruments and tubing sets are organized and placed in mating recesses of the pack so that the pack can act as a tray for at least some of the instruments in surgery.

A sterile field is generally established for many medical procedures. Such a sterile field can be used to maintain the instruments, medications, and other devices in a sterile condition. For example, in surgical procedures, the sterile field is typically defined by the area adjacent the surgical site that is covered by a sterile drape and the area where the previously sterilized surgical instruments and materials are placed for access by the surgeon during surgery.

In general, surgical instruments and medications that are to enter the body (such as the bloodstream, or penetrating the skin) must be sterilized to a high sterility assurance level. Further, the preparation of injectable medications and intravenous solutions requires not only a high sterility assurance level, but also well-designed containers to prevent entry of adventitious agents after initial product sterilization. In addition, such instruments and medications must be maintained in a manner to remain sterile prior to use.

SUMMARY

There exists a continuing need for improvements in surgical packs and surgical trays and systems. There also exists a continuing need for improvements in systems and methods to maintain sterility of the sterile field while simplifying the number of people and systems needed for a procedure. According to some embodiments a surgical tray can function as both a pack to transport surgical materials and devices to a surgery site and as a sterile tray for receiving a plurality of surgical instruments. The sterile surgical tray and system can also provide sterile tools and instruments associated with a surgical procedure and can reduce the need for sterile assistants to the surgeon or additional hardware.

A surgical apparatus for use by a surgeon during a surgical procedure can comprise a sealed sterilized surgical pack and a control unit. The sealed sterilized surgical pack can include a plurality of surgical instruments and a surgical tray. The surgical tray can have many shapes such as being substantially shaped to fit around the body part to be operated on. The surgical tray can have a top surface configured to be part of a sterile field of a surgical procedure and a side or bottom surface configured to be outside of the sterile field. The side or bottom surface can include a control unit receiver. The control unit can be configured to be received into the control unit receiver of the tray after the surgical pack has been opened. The control unit can be configured to power and control operation of at least one of the plurality of surgical instruments.

In some embodiments, a surgical apparatus can comprise a sealed sterilized surgical pack and a control unit similar to that above with a plurality of surgical instruments and a surgical tray. The surgical tray may also include one or more of the following features: a plurality of receiving structures, at least one electrical connector, at least one fluid connector, and at least one pump connected. The plurality of receiving structures can be located on the top surface, each of the plurality of surgical instruments removably positioned in a corresponding one of the receiving structures. At least one of the plurality of surgical instruments can be connected to the at least one electrical connector. At least one of the plurality of surgical instruments can be connected to the at least one fluid connector. The at least one pump can be connected to the at least one fluid connector. The control unit can be configured to power and control operation of at least one of the plurality of surgical instruments and the pump.

In some embodiments, the control unit receiver is positioned below the sterile field. The control unit may or may not be sterile. The tray can be disposable while the control unit is reusable. The plurality of surgical instruments can comprise a biological tissue cutter, and a tissue illuminator. The tray can be configured to sit on a surgical stand to the side of or on top of the patient. The procedure may be an ophthalmic surgical procedure.

A surgical apparatus according to some embodiments can comprise a plurality of surgical instruments and a surgical tray. The surgical tray can be shaped to substantially fit around the head of a patient and can include a plurality of receiving structures located on an upper side of the tray and a recess for receiving a container of fluid, each of the plurality of surgical instruments removably positioned in a corresponding one of the structures. The recess can comprise a spike for insertion into the container of fluid, and a light positioned within the recess for shining light through the container of fluid to indicate a fluid level to the surgeon. The plurality of surgical instruments and the surgical tray can be prepackaged and sterilized together.

According to certain embodiments, a surgical apparatus for use by a surgeon during an ophthalmic surgical procedure can comprise a plurality of surgical instruments and a surgical tray. The surgical tray can be substantially shaped to fit around the head of a patient. The surgical tray can include a plurality of structures located on an upper side of the tray, at least one pump, and a recess for receiving a container of balanced salt solution (BSS). Each of the plurality of surgical instruments can be removably positioned in a corresponding one of the structures. The recess can have a vented spike and a light. The vented spike can have a first channel, a second channel, and a hydrophobic filter. The first channel can be connected to the at least one pump via tubing and the second channel can be connected to the hydrophobic filter to allow air into the channel. The light can be positioned adjacent or within the recess, such as at a bottom or side of the recess, for shining light through the container of BSS to highlight the meniscus of the fluid and thereby indicate the fluid level to the surgeon.

In some embodiments, the tray is configured to sit on a surgical stand to the side of or on top of the patient. The tray may include or house a processing unit to control operation of at least one of the plurality of surgical instruments and the pump. The plurality of surgical instruments can comprise a biological tissue cutter, and a tissue illuminator. The light source of the tissue illuminator can be any type of light including a light emitting diode (LED). The light source can be any color, but in particular may be one of blue, amber, purple, and green or the like.

A surgical apparatus according to some embodiments for use by a surgeon during a surgical procedure can comprise a plurality of surgical instruments and a surgical tray. The surgical tray can comprise a substantially U-shaped cutout at the center of the tray to allow the tray to fit around the body part to be operated on of a patient. The surgical tray can have a U-shaped recess on a bottom side of the tray positioned along the U-shaped cutout. The U-shaped recess can be configured to receive a portion of a support on a surgical table or chair such as a tray support and that the tray can be attached to the tray support. Two holes in a front surface of the tray can provide access to the U-shaped recess. Each hole can be configured to receive an end of the portion of the tray support. The tray can also include a plurality of structures located on an upper side of the tray, where each of the plurality of surgical instruments is removably positioned in a corresponding one of the structures.

In some embodiments, a method of preparing for an ophthalmic surgical procedure can comprise one or more of the following steps. Removing a lid from a lip of a container surrounding a sterile bottle. Aligning the container with a recess in a sterile surgical tray, the recess configured to receive the sterile bottle. Placing the lip of the container around the recess so that the bottle can be advanced into the recess. Compressing the container such that the lip is forced into contact with the sterile surgical tray causing a side wall section of the container to collapse decreasing an overall length of the container. Inserting the bottle into the recess in the sterile surgical tray. Removing the container from covering the bottle, leaving the bottle within the recess.

Additional embodiments of a method may also include one or more of the following additional steps. Compressing the container comprising collapsing an accordion-style section of the side wall of the container. Compressing the container comprises pressing downward on a bottom surface of the container while the lip is in contact with the sterile surgical tray. Puncturing a membrane of the bottle with a spike positioned within the recess. Advancing the bottle onto the spike in the recess. Discarding the container.

A method of preparing for an ophthalmic surgical procedure according to some embodiments can comprise one or more of the following steps. Removing a lid from a container holding a sterile bottle of balanced salt solution. Inserting the bottle of balanced salt solution into a recess in a sterile surgical tray. Collapsing an accordion-style section of a cylindrical side wall of the container by pressing on a bottom surface of the container while a top lip surface engages a rim on the recess in the tray. Removing the container from covering the bottle of balanced salt solution, leaving the bottle on the tray. Discarding the container.

The method may also include one or more of: puncturing a membrane of the bottle of balanced salt solution with a spike in the recess and advancing the bottle of balanced salt solution onto the spike in the recess.

In some embodiments, an apparatus for use in preparation for an ophthalmic surgical procedure can comprise a container having an internal chamber, a lid on the container, and a bottle of balanced salt solution positioned within the internal chamber. The container can have a generally cylindrical side wall including a collapsible/expandable section that can change the length of the container. The container can be configured to collapse as the bottle of balanced salt solution is inserted into a receptacle of a sterile tray.

In some embodiments, the collapsible/expandable section comprises an accordion shaped section. The lid can be a TYVEK lid or other similar material.

BRIEF DESCRIPTION OF THE DRAWINGS

Various embodiments are depicted in the accompanying drawings for illustrative purposes, and should in no way be interpreted as limiting the scope of the inventions, in which like reference characters denote corresponding features consistently throughout similar embodiments.

FIG. 7 is the bottom of the tray of FIG. 3.

FIGS. 24-27 illustrate part of a method of using a sterile bottle container.

DETAILED DESCRIPTION OF THE PREFERRED EMBODIMENT

The following description will be disclosed for illustrative purposes relative to ophthalmic surgery but those skilled in the art will appreciate that the embodiments as described herein and as claimed may equally apply to other types of surgery and medical procedures.

A sterile surgical tray and system can beneficially provide a user such as a doctor, surgeon, or nurse with the instruments, tools, and/or materials that are needed for a medical procedure. The surgical tray and system can provide the needed elements in a sterile manner and in a configuration that is ready to use after opening of the tray. The tray and system can be designed for a particular type of medical procedure and can allow the doctor, surgeon, nurse to perform the procedure without having to obtain other materials, or only requiring a minimal amount of other materials and/or assistance to allow the surgical procedure to be performed outside of an operating room, for example, in a doctor's office or a military operating room war setting. For example, the tray and system can provide all necessary surgical tools for an operation, as well as power and control systems for those tools. Additionally, the tray and system can provide the tools in a ready to use configuration, such as already plugged in to power connectors, fluid connectors, aspiration connectors, etc. As another example, the tray and system can include a disposable tray with all of the necessary surgical tools for an operation, and a reusable control box/unit that can be plugged into or otherwise connected to the disposable tray.

In addition to providing necessary materials on a sterile tray that can be used during the procedure, the tray and system can provide additional benefits. For example, the tray can provide the materials organized in a manner that has been optimized for the procedure. As another example, the tray can allow the user to perform the procedure without requiring an assistant to help organize, obtain, and/or provide the materials to the user. This can simplify the procedure as well as greatly reducing the cost of the procedure. The tray and system can also allow a non-sterile assist to prepare the surgical tray and system without compromising the sterile field, including connecting the control system and connecting a container of balanced-salt solution (BSS) to the tray.

Figure 1:
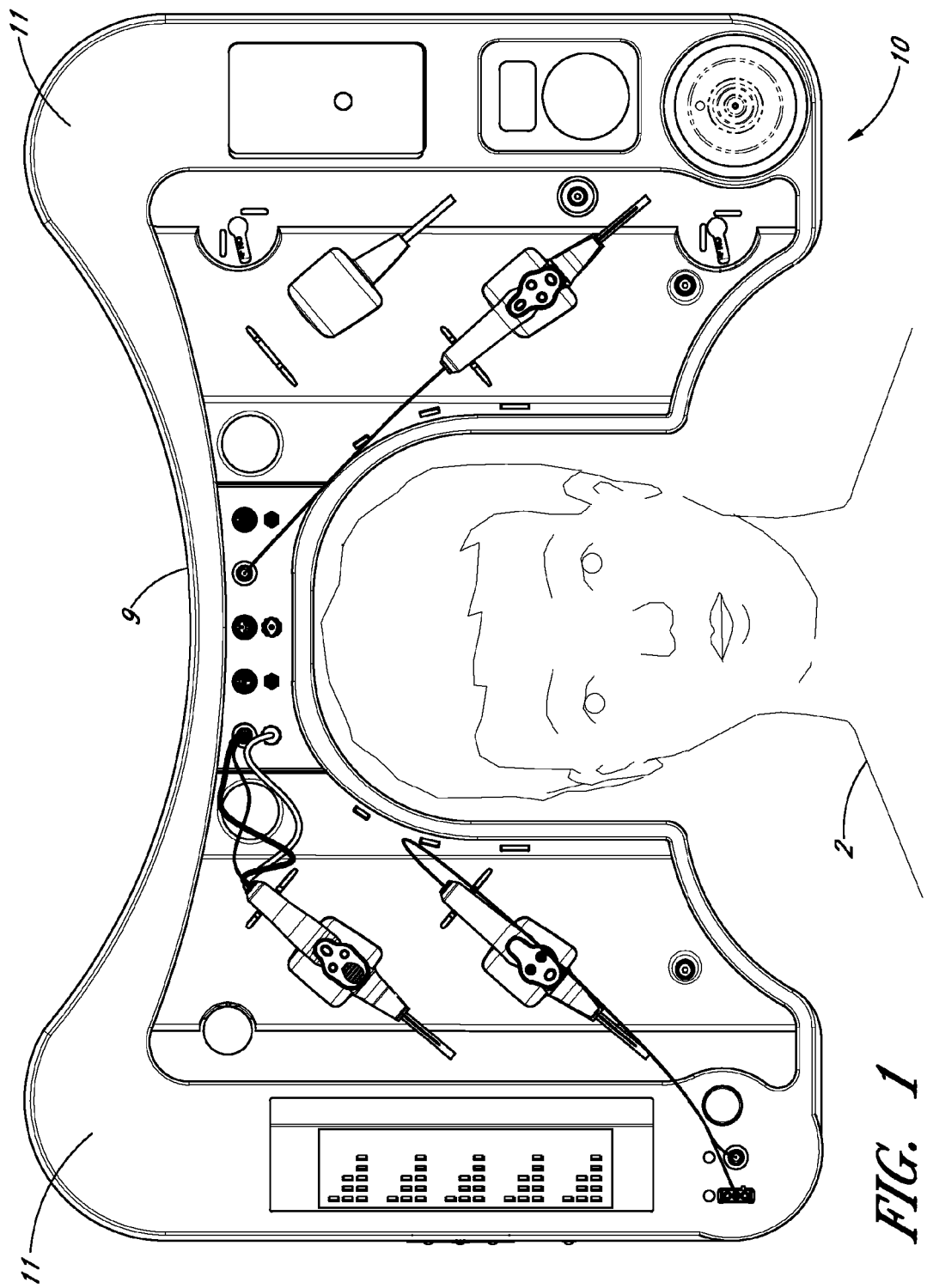
FIG. 1 illustrates a patient in position for a surgical procedure.

By way of example, FIG. 1 shows a patient 2 lying down on his or her back with a surgical tray 10 surrounding the head of the patient 2. Such a patient can be prepared for a surgical procedure, including an ophthalmic procedure on one or both eyes of the patient. In this type of procedure, the tray 10 can be part of the sterile field and can contain or hold instruments and/or medications that have previously been sterilized.

In general terms, a surgical tray can provide rapid access to packaged components without requiring the transfer of the components to a separate tray or table. In this regard, the surgical tray, upon opening, serves as a sterile tray for a surgical procedure. The surgical tray can contain instrumentations ready for use already setup on the tray. The instrumentations can be positioned at suitably convenient locations from which the surgeon can remove, use, and put back the instrumentation when not in use.

The tray can be a sterile surgical tray that has been manufactured and assembled as a prepackaged sterile pack that functions as a tray during surgery. The term pack is meant to collectively identify the surgical instruments and other items contained in a sterile package that is shipped from the manufacturer to a customer, such as a hospital, ambulatory surgery center, doctor's office, military setting, etc. and is for use by a surgeon, doctor, nurse, etc. to perform a medical procedure, such as surgery. The term tray refers to a structure that defines at least a portion of a surgical field and can hold fluid handling devices, surgical instruments, and other miscellaneous items to be used during surgery.

In a preferred embodiment, the pack can be synonymous with the tray. The surgical tray may be manufactured and assembled with the necessary equipment for surgery and then enclosed in a bag or other container and sterilized. Then when the bag is opened, the tray is removed from the bag, a lid or cover is potentially removed, revealing several if not all the instruments and other items needed for the medical procedure, such as surgery.

The tray 10 may take the place of a traditional Mayo tray and may be placed between the surgeon and the surgical site. During an operation, after the pack is opened by removing the covering or removing the tray from an enclosure, the tray 10 may be placed at the left or right side of the surgeon, on or over the patient's chest, or on another surgical apparatus such as a surgical stand in close proximity to the surgeon and the patient. The tray can also be positioned between the surgeon and the head of the patient.

The tray can surround the head, or other desired area of the patient where the procedure is to be performed. For example, the tray can surround the head of the patient 2 to thereby position the tray around the head of the patient and between the surgeon and the head of the patient. In such a configuration, the tray can also define and/or confine the sterile field by surrounding the head or other desired area and limiting access thereto.

The tray can be placed on or attached to a structure surrounding or near the surgical bed, chair, table, etc. The tray can be connected to or placed on a structure such as a rail system, a stand, a tower, a bed side, a cart, a table, etc. For example, in some embodiments, the tray is configured to attach to an arm or wrist support attached to a surgical chair. The tray itself can then be used as both a tray and a wrist or arm support.

Wrist supports are commonly used in many procedures, especially procedures on the eye where precision and a steady hand is needed. A wrist support and/or the tray can be adapted to allow the wrist support to be used to support the tray. Thus, the wrist support 12 is repurposed here as a tray support. The tray can then provide support for users wrists and/or arms.

Figure 2:
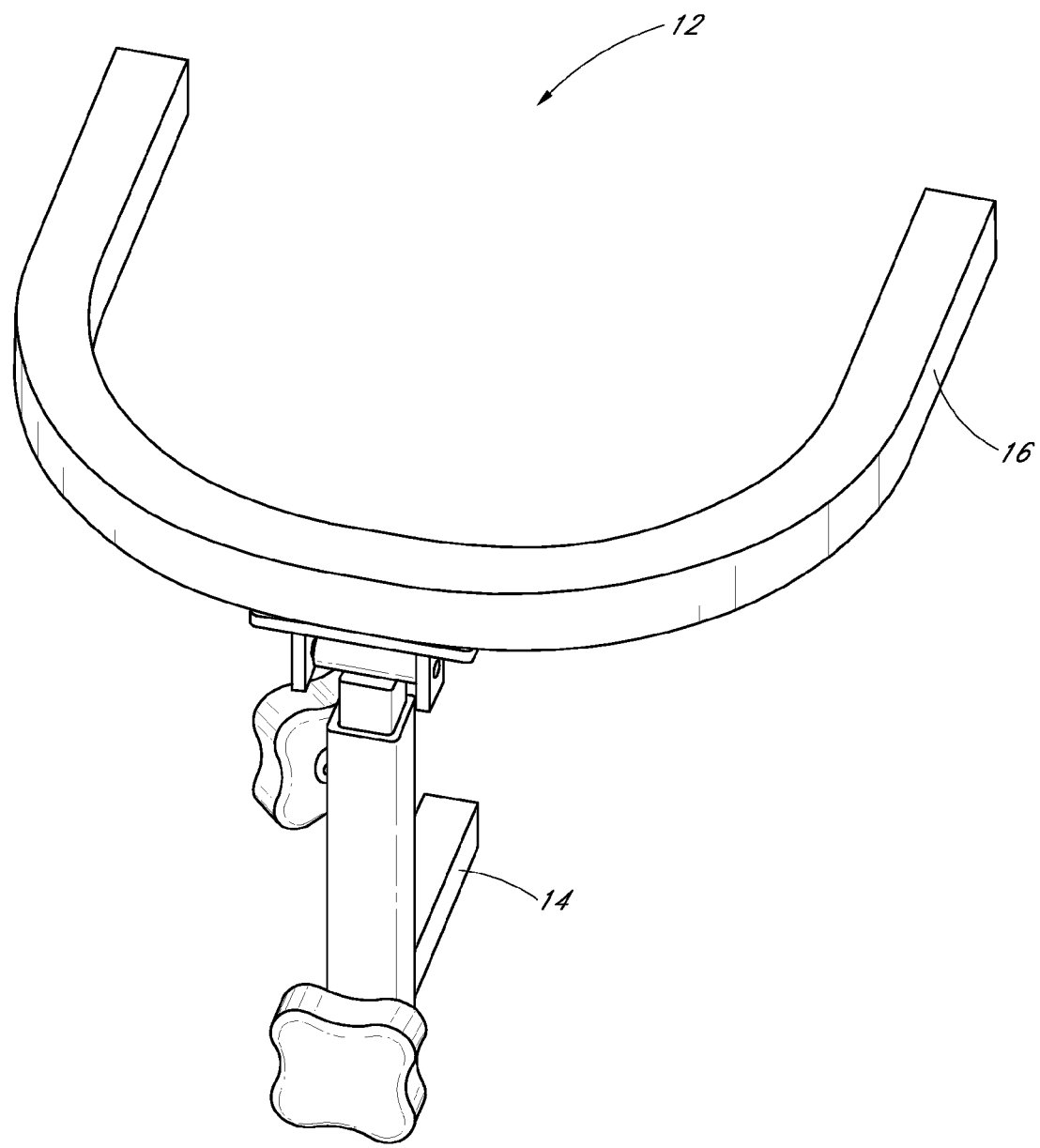
FIG. 2 shows a tray support.
Figure 3:
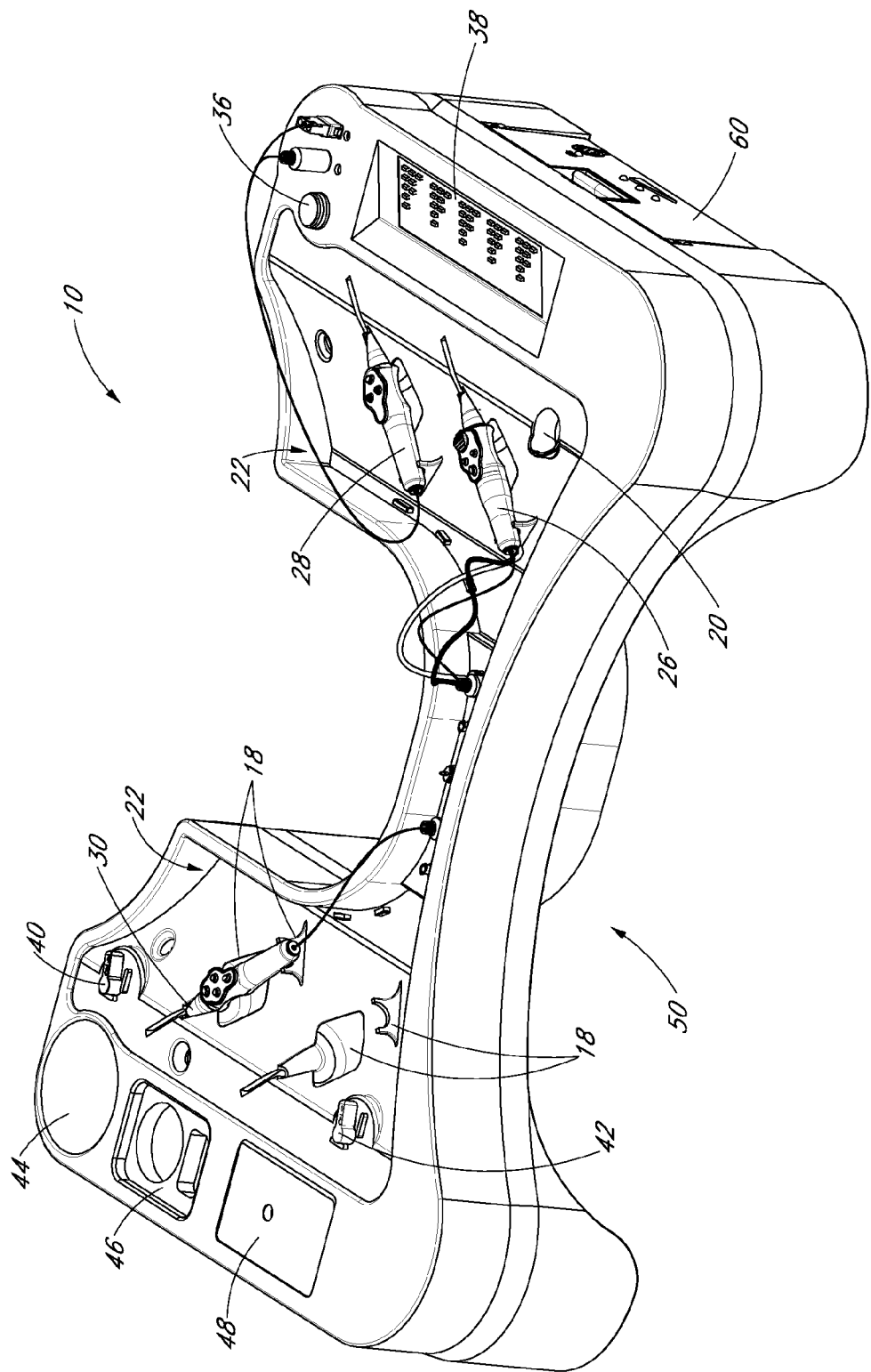
FIG. 3 is a perspective view of a tray.

FIGS. 2 and 3 show respectively, a tray support 12 and the tray support 12 mounted to a headrest of a surgical table or chair 13. A patient lying on the table 13 can have his or her head positioned on the headrest such that the tray support 12 surrounds the patient's head. This can provide a support for the doctor, surgeon, nurse, etc. to rest or steady the hands or arms during a procedure.

A tray 10 placed on the tray support 12 can surround a patient's head as shown in FIG. 1. The tray 10 can surround the patient's head while still providing support to one or more of a user's wrists and/or arms. For example, a surgeon could rest his or her forearms on the support portions 11 of the tray 10. The support portions 11 can be free of instruments, tools or other features so that the surgeon is free to rest and reposition his or her arms on the support portion 11 without interference from other features.

In some embodiments, the support portion 11 is raised up higher than some other parts of the tray. The support portion 11 may be substantially flat. In some embodiments, the support portion 11 can be an elongated protrusion with a rounded or flat top surface above the other surfaces of the tray 10. In some embodiments, the support portion 11 can be configured to be positioned at the sides of the doctor, so that the doctor can be positioned closer to the patient with his or her elbows or forearms supported at his or her sides and at the sides of the tray. The tray 10 is shown with an inward contour 9 that allows the body of the doctor to be closer to the patient while his or her arms are supported at the sides of the body and possibly near the back of the doctor's body.

Figure 2A:
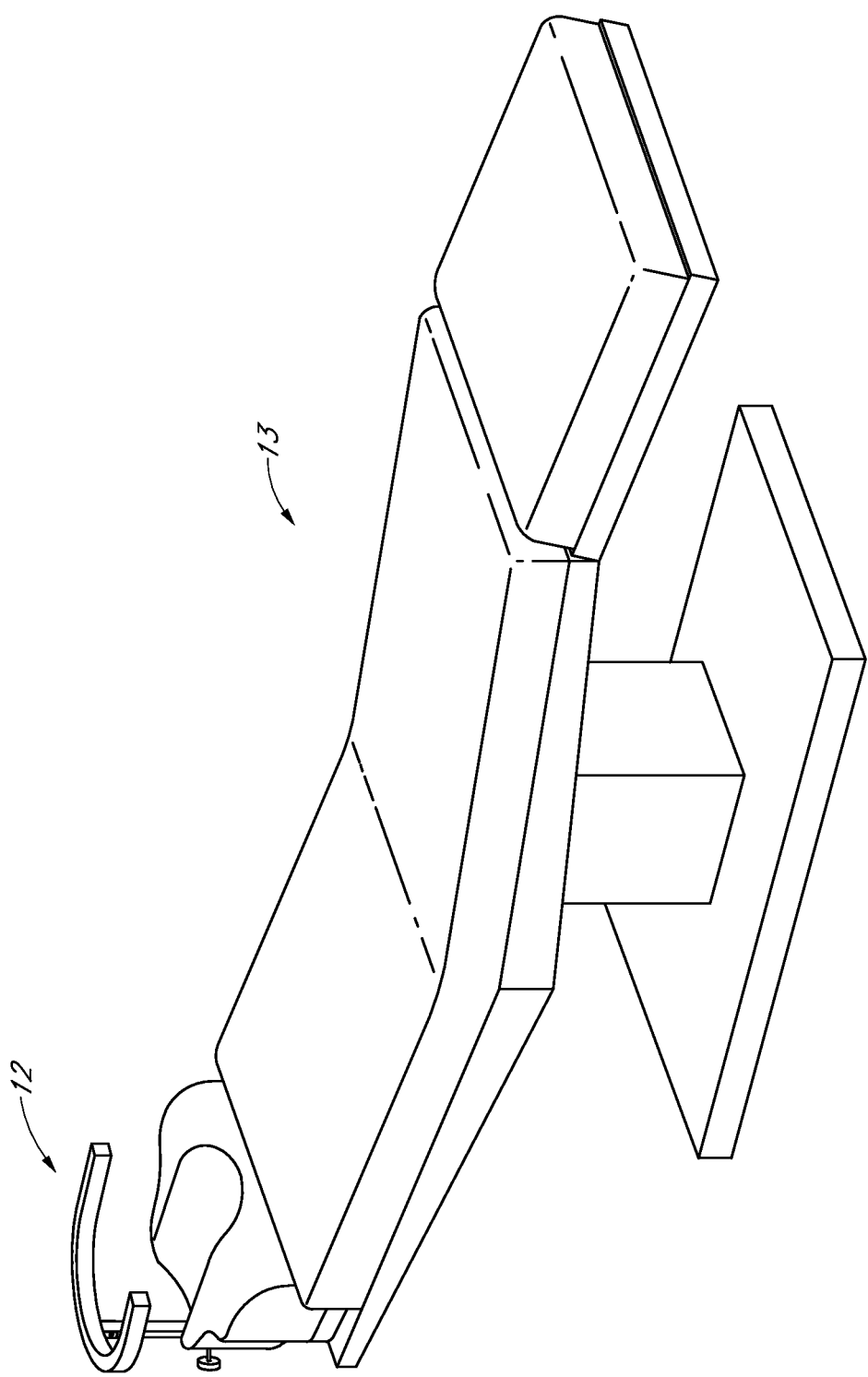
FIG. 2A shows a surgical chair or bed with a tray support.

Returning to FIG. 2, an example tray support 12 is illustrated. The tray support 12 can also be used for positioning a tray 10 within the surgical field. The illustrated tray support 12 can connect to a surgical stand, table, chair 13, etc. at end 14, as shown in FIG. 2A. The tray support 12 can have a top support bar 16, such as the illustrated U-shaped ring. The support bar 16 can have a fixed or adjustable relationship to the surgical stand, table, chair 13, etc. to which it is attached. The support bar 16 can have one of many different shapes. For example, the support bar 16 can be circular, semi-circular, U-, V-, or L-shaped, or a box with three sides. The support bar 16 can be made of a round or square bar, tube, or pipe. As illustrated, the support bar 16 is made of a square tube formed in a U-shape.

Figure 2B:
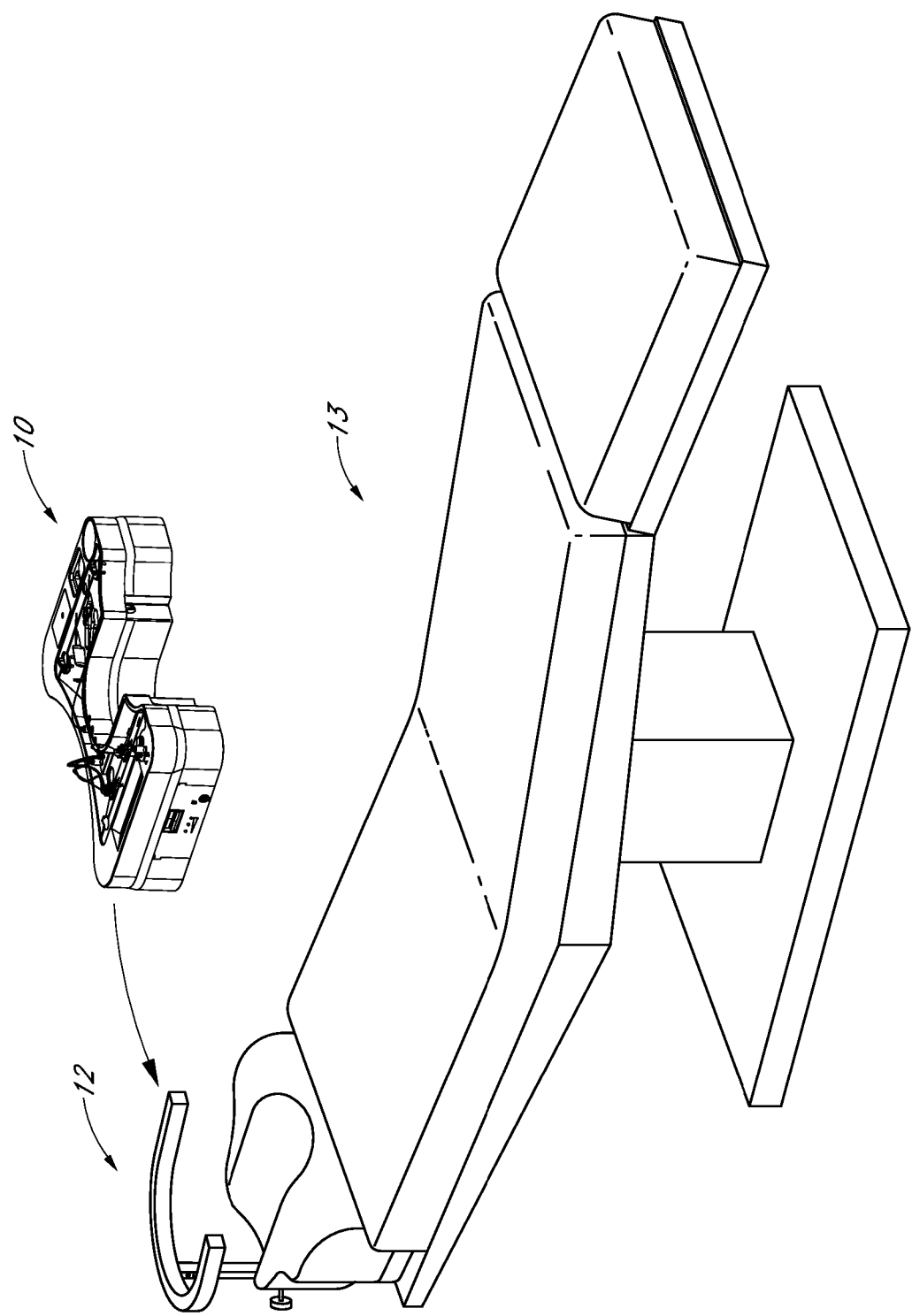
FIG. 2B shows a surgical chair or bed with a tray support and a tray.

As has been mentioned, the tray 10 can be placed on or attached to structure surrounding or near the medical bed, chair 13, or table such as on the support bar 16 of the tray support 12. The tray 10 can be placed on, slid onto, or otherwise secured to the support bar 16 (FIG. 2B). The tray 10 can attach to the support bar 16 or other structure in one of many different ways.

Looking at FIGS. 3-6, the contour and shape of the tray 10 can be seen. The tray 10 can be shaped to not only surround a head or other desired area of a patient, but also to allow a particular positioning of the surgeon with relationship to the patient. For example, the tray can be positioned between the surgeon and the patient while also placing some or all of the instruments off to the sides of the patient. The instruments can also be within the doctor's peripheral vision. The shape of the tray 10 can also facilitate attaching the tray to a particular structure such as a tray support 12.

The shape of the tray 10 can optimize the utilization of available space next to or around the area of the patient 2 to be operated on. For example, around the patient's head, the combined tray 10 and the tray support 12 can allow the surgeon to be sufficiently close to the patient while providing all of the necessary instruments within short reach of the surgeon. In addition, while utilizing the tray 10, the surgeon generally does not need to even turn to the side or extend his or her reach as the instruments are at hand right where they are needed.

Figure 5:
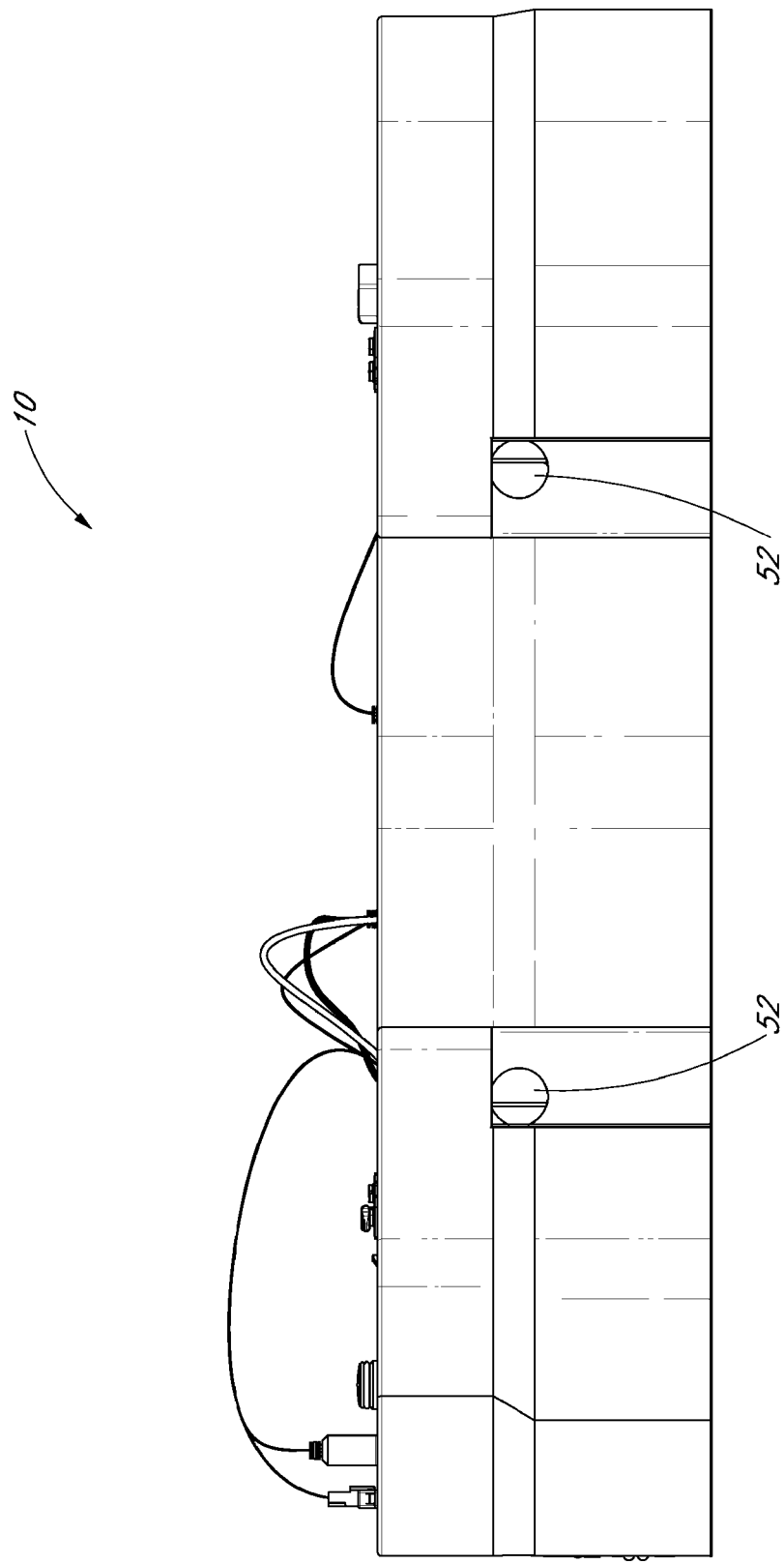
FIG. 5 shows a front view of the tray of FIG. 3.
Figure 6:
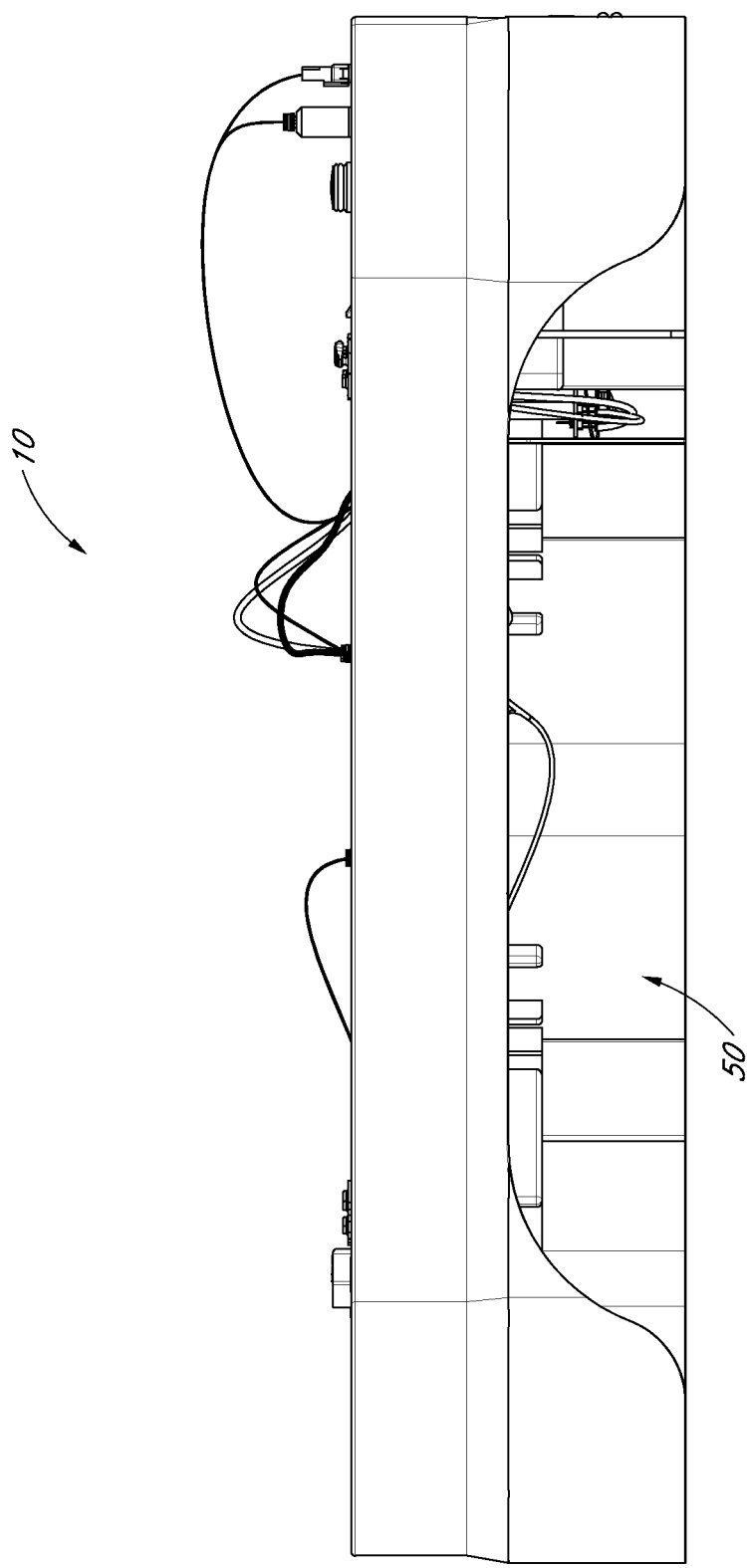
FIG. 6 shows a back view of the tray of FIG. 3.

For example, as shown in FIGS. 3 and 6, the back of the tray 10 can include a cutout 50 that can, for example, allow for more room for the surgeon's legs or body beneath the tray 10. The back (FIG. 6) of the tray is closest to the body of the surgeon and the front (FIG. 5) is the side closest to the patient (see FIG. 1), where the surgeon is sitting or standing directly behind the top of the patient's head. The cutout 50 can also provide additional visual access below the tray 10 to assist in mounting the tray 10 to an appropriate structure, such as the support bar 16 on the tray support 12.

Figure 7A:
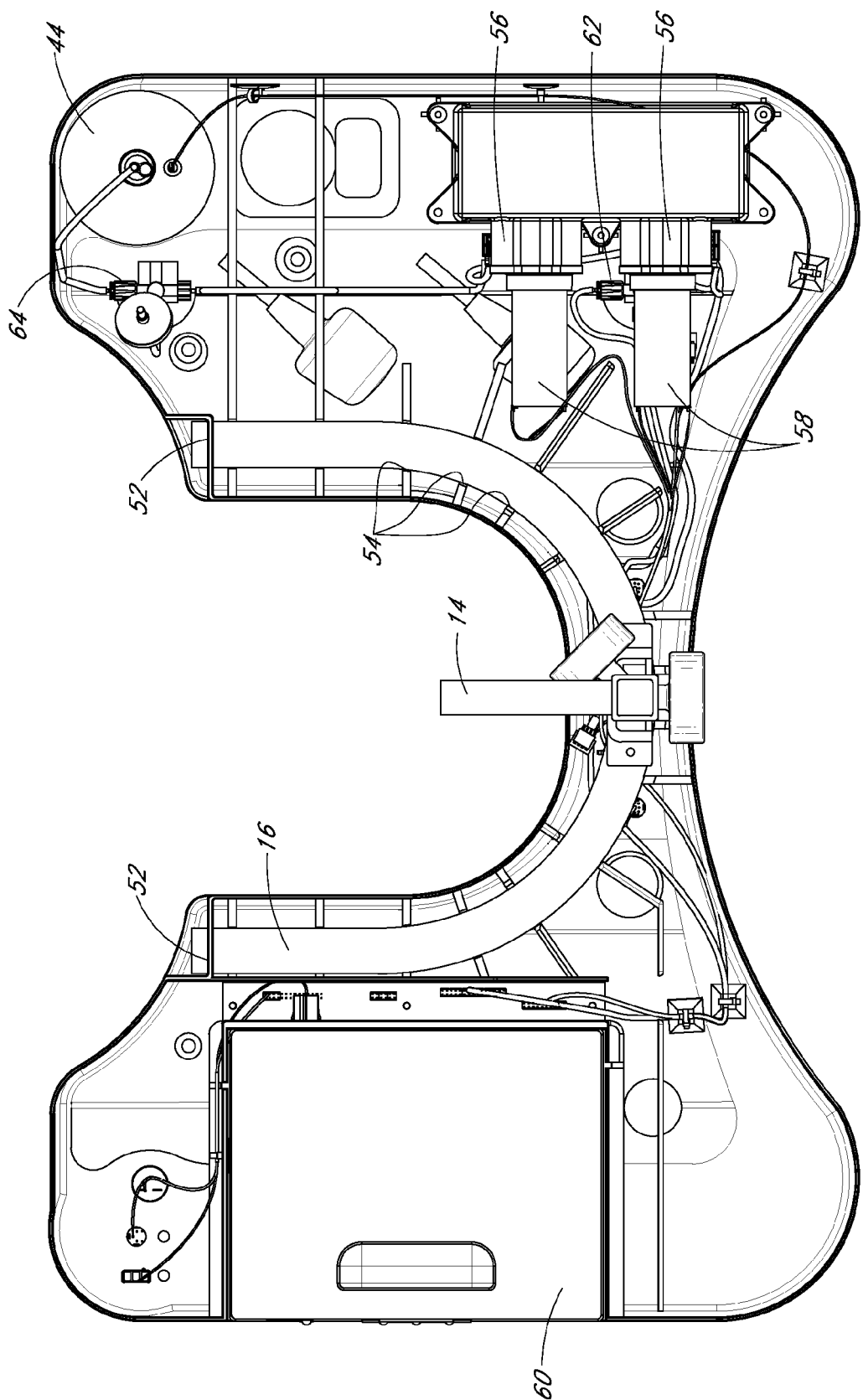
FIG. 7A shows a bottom view of a tray connected to a tray support.

The bottom of the tray, as shown in FIGS. 7 and 7A, as well as other portions, can be shaped and/or contoured to facilitate attachment to particular structures such as the support bar 16. The tray 10 can include a slot or space 54 sized to allow the tray 10 to fit on top of the support bar 16 of the tray support 12 (FIG. 7A). The slot 54 is shown formed across the various support ribs on the underside of the tray 10. The slot can also be formed in other ways. The slot 54 or other attachment structure can allow the tray to attach to and/or cover all or only part of the support bar 16.

In the front view of FIG. 5, it can be seen that the tray 10 can also include one or more holes 52. The holes 52 can cooperate with the slot 54 cut into the supporting ribs on the underside of the tray 10 (FIGS. 7 and 7A) to fit over and onto the support bar 16. The holes 52 can be one of many different shapes. For example, the holes 52 can be round (as shown), or square. In addition, the holes can be shaped to work with different shaped and/or sized support bars. For example, in the illustrated embodiments, the holes a round and the support bar has a square cross-section. In some embodiments, the holes and the support bar have corresponding shapes.

The tray 10 may include one or more mechanisms for latching of the tray onto a surgeon's chair, a surgical platform, a separate stand, wrist support 12, support bar 16, etc. The latching mechanism may include, for example, a snap fit, a screw, a lock, a spring loaded locking handle, etc. Additionally, the slot 54 can be tight fitting over the support bar 16 to minimize and possibly prevent undesired movement of the tray. In some embodiments, the slot can be a deep slot that extends the entire height of the support bar 16. The slot may also include one or more tabs that extend around a portion of the underside of the support bar 16.

The tray 10 is preferably secured to or positioned on the support bar 16 in a manner to not tip, tilt, or fall off the support bar 16 when the tray experiences downward or sideways pressure on any point of the tray.

The illustrated tray 10 can be mounted onto the support bar 16 as follows: 1) the tray 10 is placed over the support bar 16 such that the front of the tray is forward of the front ends or top of the "U" of the support bar 16, 2) when the holes 52 are near the front ends or top of the "U" of the support bar 16 the front of the tray is tilted downwards and the tray is advanced backwards onto the support bar 16, with the front ends or top of the "U" of the support bar 16 advancing through the holes 52, 3) the tray is then slid backwards onto the support bar 16 until the entire length of the slot 54 is substantially positioned over the support bar 16, 4) the tray 10 is un-tilted or straightened by lowering the back of the tray, thereby placing the tray completely on the support bar 16. The curved shape of the support bar 16, the holes 52 and the slot 54 all cooperate to maintain the tray on the support bar 16 such that the tray will not be easily displaced from, tipped over, or titled on the support bar 16.

Returning now to FIGS. 3 and 4, features relating to the use of the sterile surgical tray 10 will now be discussed. The tray 10 includes receiving or mating structures 18 for receiving a plurality of surgical instruments. The receiving or mating structures 18 for receiving the instruments may generally conform to the shape of a particular instrument or may be general areas where instruments can be placed or held that does not have a specific structure for a specific instrument. As used herein the term "mating" means without limitation a receptacle having a complementary shape for receiving part or all of an article. The mating structure 18 can include a recess or cavity in the tray 10 having a shape that may hold a variety of instruments. The mating structure 18 can have a protrusion, a cradle, a guide member, or other structures which receive and/or position an instrument on the tray 10.

The tray 10 can have sufficient area on the top surface to receive the surgical instruments necessary for the surgery to be performed with sufficient space between the instruments to allow the surgeon to easily and conveniently pick-up an instrument and return it to the tray 10.

The tray and/or pack can include a number of different surgical components which may be prepackaged and sterilized with the tray 10. For example, surgical components of the surgical pack can include: a biological tissue cutter, a tissue illuminator, an aspiration/infusion device, a disposable speculum/drape combination, cotton swabs, a container containing BSS, an infusion line, trocars, cannulas, forceps, etc.

If the sterile surgical tray 10 is for ophthalmic surgery the surgical instruments preferably include at least a biological tissue cutter, an aspiration instrument, and an infusion instrument. The biological tissue cutter may be at least one of a vitreous cutter, a lens emulsification, fragmentation, or cutting device, scissors, and a cautery knife. Aspiration may be incorporated into the biological tissue cutter, such as is known in vitreous cutters and phacoemulsification (phaco) devices. The aspiration and infusion instruments may be a combined infusion and aspiration instrument, commonly referred to as an irrigation/aspiration (I/A) handpiece. If the surgical tray 10 is for vitreoretinal surgery the infusion instrument may be an infusion cannula with connected tubing.

Preferably tray 10 includes all or nearly all the instruments necessary to perform the desired surgery. For instance, if the desired surgery is a vitrectomy of the eye, it can include a vitreous cutter, an irrigation instrument, an illumination instrument, an aspiration source, an infusion source, and passive surgical instruments (for example, not powered), and possibly an air/fluid exchange source. If the desired surgery is a cataract removal from the eye, the instruments included in the tray can be cataract extraction instruments such as a phaco device, a phaco needle, a capsule polish tool, an aspiration source, an infusion source, and passive surgical instruments, and possibly an oil filled syringe.

Figure 4:
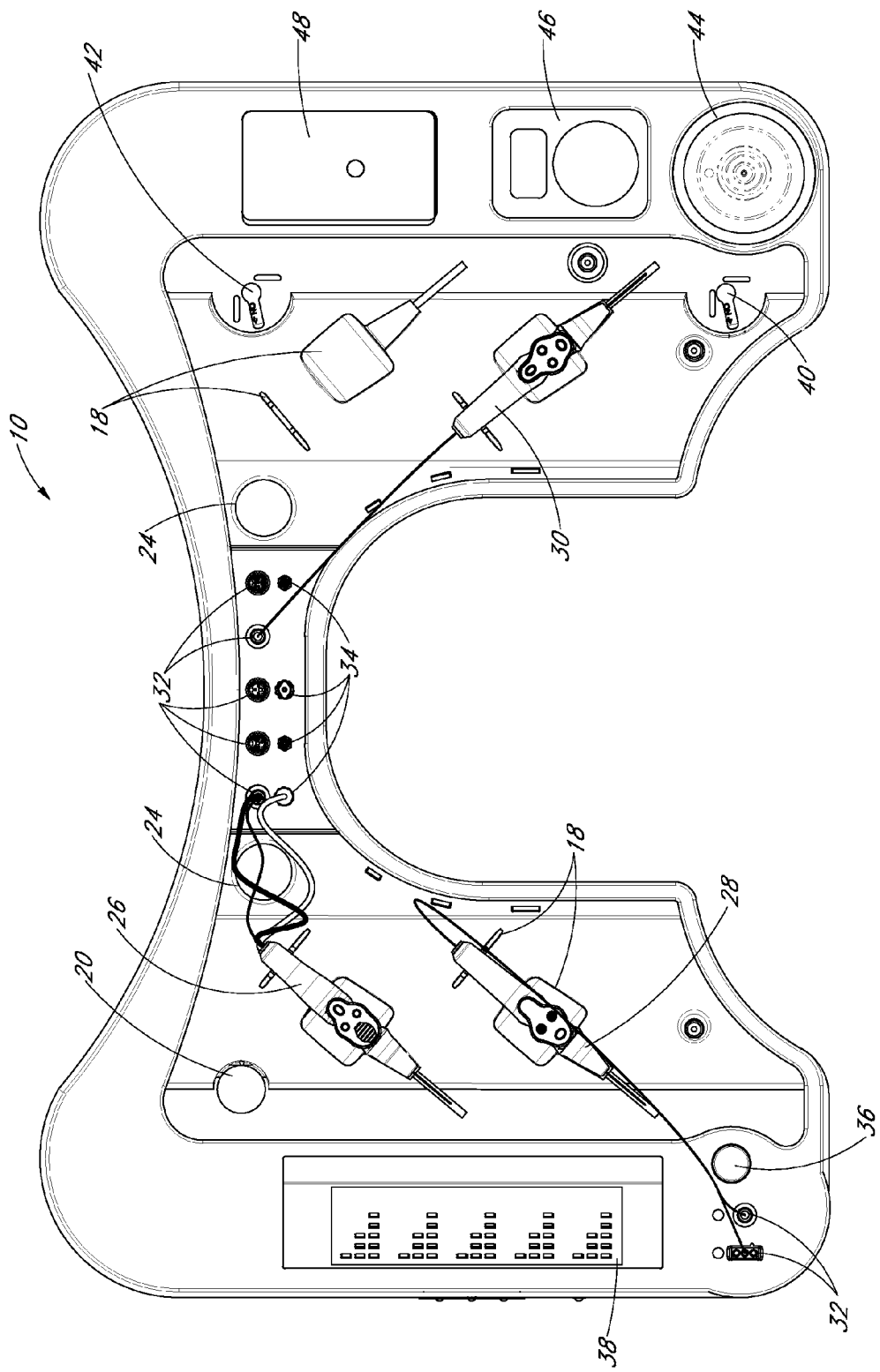
FIG. 4 shows a top view of the tray of FIG. 3.

In the illustrated embodiment of FIGS. 3 and 4, the tray 10 can be used for ophthalmic surgery and includes a vitreous cutter 26, a diathermy or electrocautery device 28, and an illumination device 30. The diathermy or electrocautery device 28 can be used to stop bleeding from small vessels by destroying tissue using heat conduction, as is known.

Tray 10 also preferably includes structure for receiving additional instruments beyond the plurality of instruments that are prepackaged and sterilized with the tray 10; an example of which is the structure 18 shown without any instrument thereon.

Also, at least one surgical instrument may be connected at manufacture to the tray 10 at various electrical, and/or fluid connections. As best seen in FIG. 4, the tray 10 includes various electrical connectors 32, as well as various fluid connectors 34. The electrical connectors 32 can be used to connect the surgical instruments to various features such as a power source and a controller. The fluid connectors 34 can be used to connect the surgical instruments to various sources including fluid and vacuum sources.

Tray 10 may include structure forming a priming fluid reservoir 20 for receiving one or more instruments during priming of the instruments with a surgical fluid such as balanced-salt solution (BSS). If a reservoir is not provided the user may need to use a beaker or other container for priming the surgical instruments and tubes with BSS. Fluid reservoir 20 can be a self filling fluid reservoir 20. The fluid reservoir 20 can fill such as during a self check procedure after the control system has been turned on. Self filling can be a step in the start up routine of the controller. The fluid reservoir 20 can fill with BSS.

The tray 10 can have a recessed top surface forming one or more troughs 22, as best seen in FIG. 3. The tray 10 can also include one or more fluid wells 24 as best seen in FIG. 4. The trough 22 and fluid well 24 can be used to retain fluid such as fluid ejected or leaked from the instruments and fluid runoff from the surgical procedure.

A drape can be placed over a patient, such as over a portion of a patient's head (not shown) during ophthalmic surgery. If desired, the drape can be attached to the tray 10 by any suitable structure such as adhesive tape, hook and loop material, or other structure. Fluid runoff from the drape that occurs during surgery can be controlled using at least one fluid retention trough 22 and/or fluid well 24 to collect the fluid.

Additional features, shown in FIGS. 3 and 4, some of which are described in more detail below, include: power button 36, indicator panel 38, air infusion control 40, oil infusion control 42, fluid reservoir receiver 44, recessed storage bins 46 for trocars and other tools, and an aspirant fluid container 48. The aspirant fluid container 48 can receive fluid aspirated from the surgical site. In some embodiments, the aspirant fluid container 48 can include a colored float, ball, or bobber that floats at the fluid surface to indicate the fluid level. The aspirant fluid container 48 may also include a light. The light can function similar to the light in the fluid reservoir receiver 44 as described below.

The indicator panel 38 may include at least one status indicator. The status indicator can take many forms including a light emitting diode (LED), a display, numbers, icons, bar graphs, and/or an audible signal generator. In FIGS. 3 and 4, five groups of status indicators are shown. Each group of status indicators can be associated with a particular instrument or function of the tray 10. The status indicators can provide different types of feedback to a user. The status indicators can be different colors or have different numbers of lights. For example, if a fluid reservoir includes a sensor the indicators could be red, yellow, and green in color to indicate to the user that a vacuum level is unacceptable (red), a vacuum level is approaching an unacceptable level (yellow), or the vacuum level is acceptable (green). Another example is that the number of indicators illuminated can indicate the speed or energy level. The indicator panel 38 may also indicate a power level of a battery or fuel cell, a fluid level of a pump fluid reservoir attached to the input and output connectors or an illumination level of an illuminator attached to the input and output connectors.

The tray 10 may also have a control unit 60 including a processor for receiving inputs from a user, from a plurality of surgical instruments, and from other devices and for transmitting signals to the same. The control unit 60 is preferably connected to tray 10 after tray 10 is opened and is being prepared for surgery. The control unit 60 may alternatively be prepackaged and sterilized with tray 10.

As can be seen in FIGS. 3 and 4, the surgical tray 10 can provide the needed tools in a configuration that is ready to use after opening of the tray. The tray can provide these tools organized in a manner that has been optimized for the particular surgical procedure. For example, the support portions 11 can be free of instruments, tools or other features, while the some or all of the instruments are off to the sides of the patient providing easy access to the doctor or surgeon. The surgeon generally does not need to even turn to the side or extend his or her reach as the instruments are at hand right where they are needed. In addition, various features of the tray 10 have been optimally positioned. For example, the power button 36 is spaced away from the doctor and away from the support portions 11 to prevent accidental depressing of the power button 36. Also, the fluid container in the fluid reservoir receiver 44 is also spaced away from the doctor. This ensures that the bottle in the fluid reservoir receiver 44 is not in the way, but also provides line of sight access for the surgeon to be able to view the fluid level.

The panel 38 and the fluid reservoir receiver 44 can also be positioned to the outside of the tray. This can allow the surgeon to use peripheral vision or only eye movement without diverting her head, for example, from a surgical microscope. This can increase the ergonomics of the tray and decrease distractions from head movements. Additionally, the main fluid and electrical components are separated to the opposite sides of the tray 10. The power button 36, control unit 60, and indicator panel 38 are on one side and the fluid reservoir receiver 44 and the aspirant fluid container 48 are on the other side.

In certain embodiments, the sterile surgical tray 10, as best seen in FIG. 7, also includes one or more pumps 56. As shown, each pump 56 is driven by an electric motor 58. The one or more pumps 56 can be used for various purposes, such as to provide aspiration, to provide a pressurized source of fluid, to remove material from the eye, etc.

A pump 56 can be an infusion pump operatively connected to the fluid reservoir or receptacle receiver 44. The fluid reservoir receiver 44 may be for receiving a fluid reservoir (described and shown below) for infusing fluid such as a surgical irrigation solution into a surgical site. A pump 56 can be an aspiration pump for collecting aspirated tissue and fluid during surgery. In some embodiments, the aspiration pump can pump aspirated tissue and fluid into the aspirant fluid container 48. The pump 56 may be one of a vacuum pump (for example, a rotary vein or diaphragm) or a positive displacement pump (for example, peristaltic or scroll).

Tray 10 may also include a syringe pump (not shown) for injecting oil or other fluids into the eye. With reference to FIGS. 4 and 7, the syringe pump can connect to one of the fluid connectors 34 and possibly to one of the electrical connectors 32. In particular, one of the fluid connectors 34 can be connected to the oil infusion control 42. The oil infusion control 42 can be used to control the flow of oil. The oil infusion control 42 as shown is the handle of a stopcock 62, but the control 42 can include a pump and/or solenoid valve. The stopcock 62 can be fluidly connected to one or more of the fluid connectors 34, and/or a surgical instrument.

The infusion pump 56 can also be connected to a stopcock 64. The stopcock 64 can be connected to the fluid reservoir through a fluid reservoir receiver 44. The stopcock 64 can be used to inject air into the eye during a procedure. For example, after fluid has been removed from the eye, air can then be injected into the retina during all or part of a procedure on the retina. The stopcock can control whether fluid or air is injected by an instrument such as the vitreous cutter 26. The air infusion control 40 as shown is the handle of a stopcock 64, but the control 40 can include a pump and/or solenoid valve.

The infusion pump 56 may also be connected to the syringe pump or an oil reservoir. Thus, the infusion pump 56 in this configuration can be connected to an infusion device that can infuse one or more of a fluid, such as balanced-salt solution (BSS); air; or oil into the eye.

Figure 8:
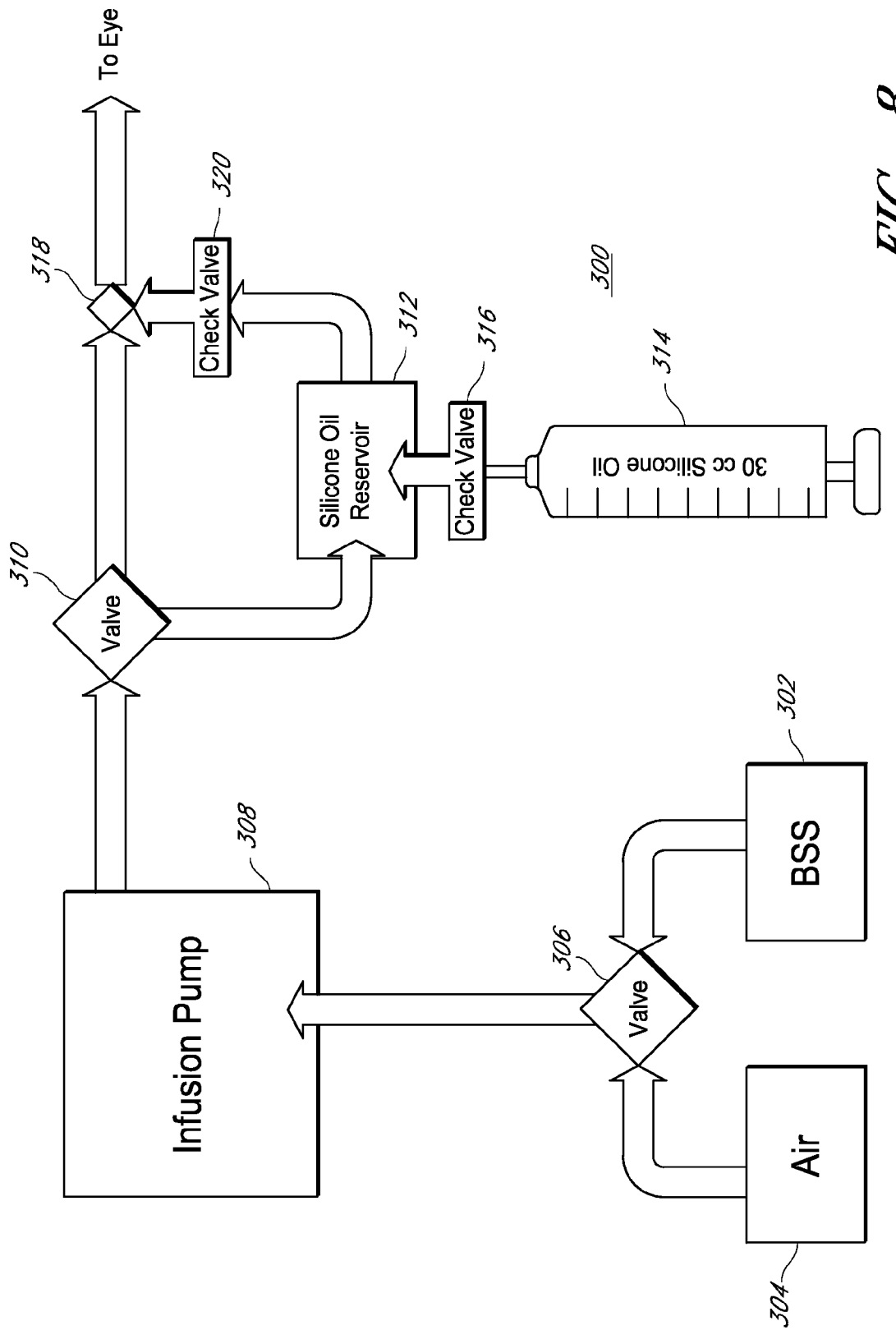
FIG. 8 is a block diagram of a fluid-air exchange system.

FIG. 8 shows a block diagram of a fluid-air exchange system 300 that may be incorporated into a sterile surgical tray, such as tray 10. System 300 preferably includes a BSS reservoir 302, a reservoir 304 of air, connected to a selector valve 306 for selecting which fluid, BSS or air, will be allowed to flow into infusion pump 308. Infusion pump 308 may be any suitable pump for infusing fluid into an eye or other body part. A bypass valve 310 connects a flow path from infusion pump 308 and an oil reservoir 312. Oil reservoir 312 is connected to a source of oil 314 via a check valve 316. Oil source 314 may be a syringe, as shown or may be another source that is connected to a pump (not shown) for automatically pumping oil into reservoir 312. Oil reservoir is then connected to a three-way stopcock valve 318 via another check valve 320. Depending on the positions of the valves 306, 310, and 318 air, BSS, or oil (typically silicone oil) will be infused into an eye. Bypass valve 310 allows infusion pump and air or BSS to push oil from reservoir 312 into an eye.

Figure 9:
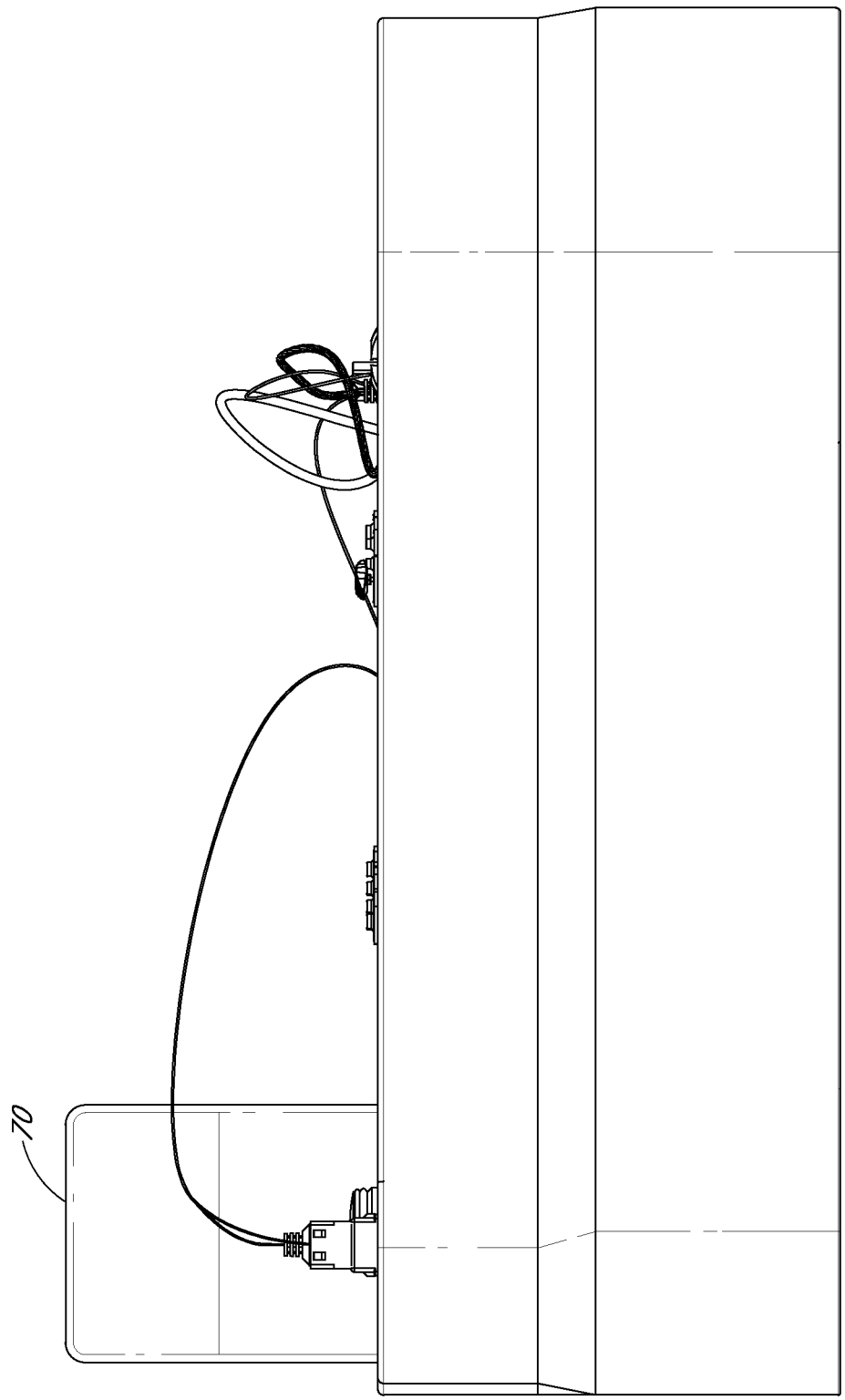
FIGS. 9 and 10 illustrate the sides of the tray of FIG. 3 with a balanced-salt solution (BSS) container connected to the tray.
Figure 10:
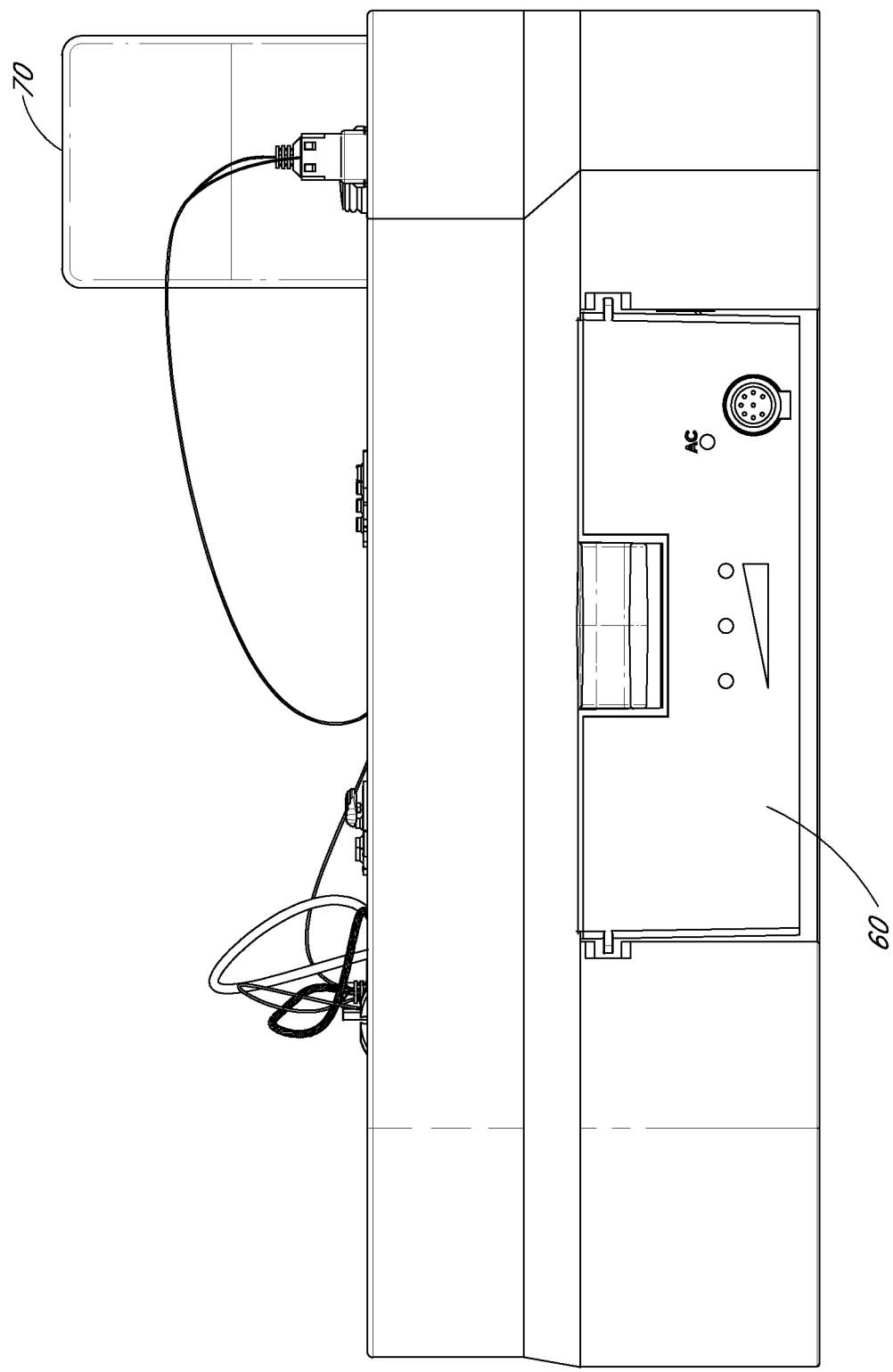

Turning now to FIGS. 9-10, the two sides of the tray 10 are shown. The tray 10 in these views also includes a BSS container 70 that has been connected to the tray 10, as described in more detail below.

Figure 11:
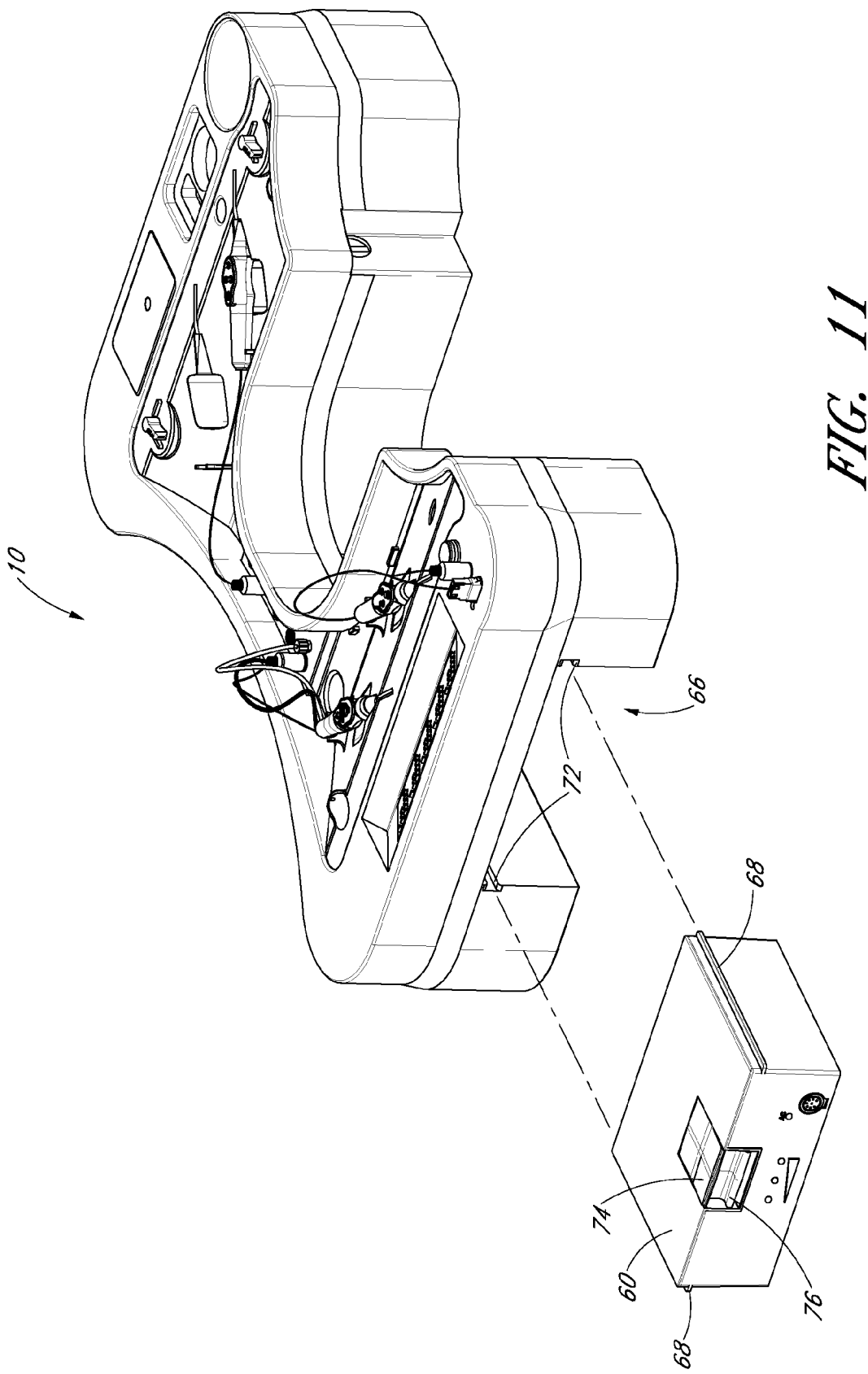
FIG. 11 shows a tray with a removable control unit.
Figure 13:
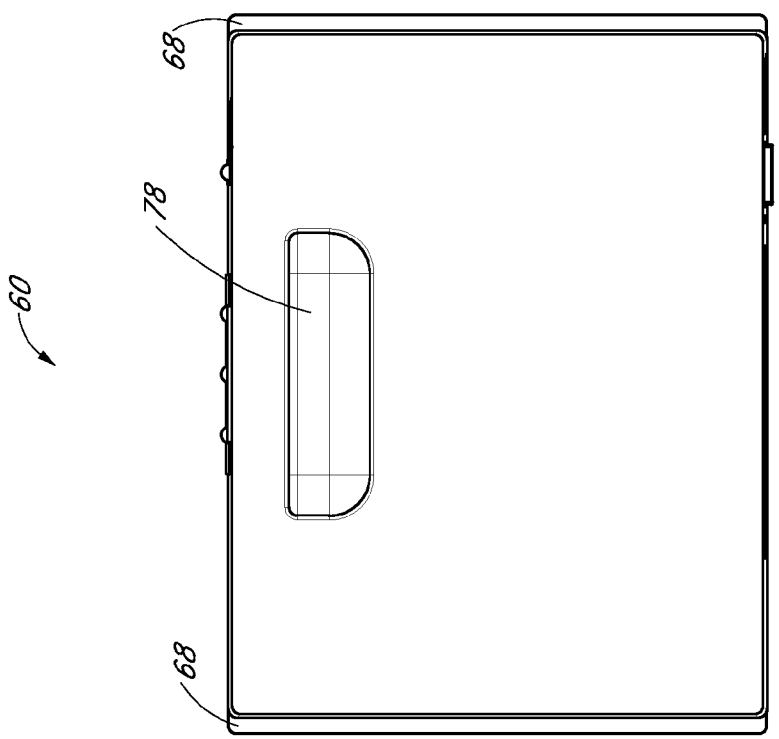
FIGS. 12-16 are top, bottom, and side views of the control unit.
Figure 12:
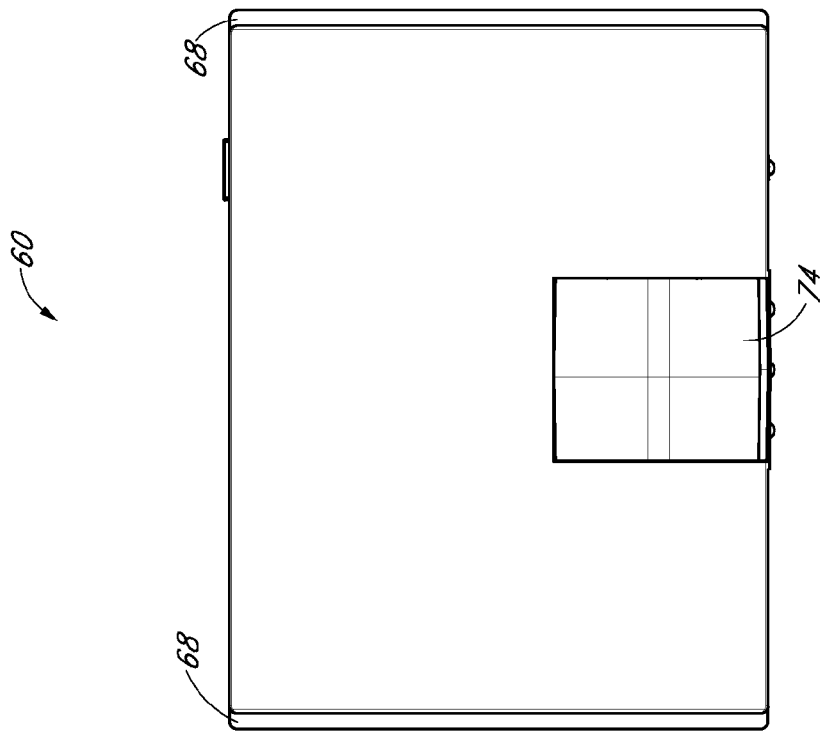
Figure 15:
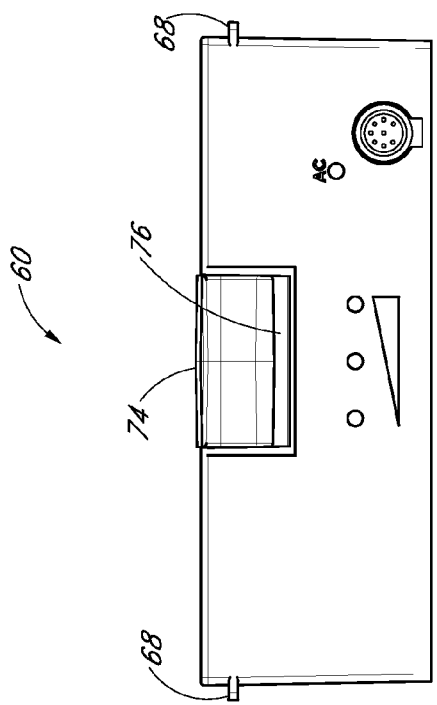
Figure 16:
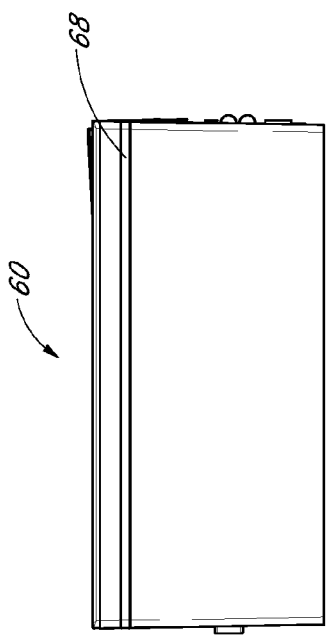

In FIG. 10, and also in FIG. 11, it can be seen that a control unit 60 may be connected to the tray 10. The control unit 60 can include a processor for receiving inputs from a user, from a plurality of surgical instruments, and/or from other devices and can transmit signals to the same.

The control unit 60 can be made as a cartridge that can be received into the tray 10. Referring in particular to FIG. 11, it can be seen that the cartridge-like control unit 60 can be inserted into a slot 66 in the tray 10.

The tray 10 with control unit 60 can provide all necessary surgical tools for an operation, as well, as power and the control systems for those tools. Additionally, the tray can provide the tools in a ready to use configuration, such as already plugged in to power connectors, fluid connectors, aspiration connectors, etc. so that once the cartridge-like control unit 60 is plugged into the tray 10 the surgeon can start the procedure with minimal to no additional preparation. The tray can be a disposable tray with all of the necessary surgical tools for an operation, and the control unit 60 can be a reusable control unit 60 that can be plugged into or otherwise connected to the disposable tray.

The cartridge-like control unit 60 can have a pair of rails 68 on the sides of the control unit 60. The rails 68 can be received by grooves 72 in the slot 66 on the tray. The cartridge can be slid into the slot 66 with the rails 68 engaging the grooves 72 until the button lever 74 engages the tray 10. The grooves and rails and/or housing shape can be arranged such that the cartridge control can only be inserted in one orientation to prevent the user from inserting the cartridge incorrectly. The button lever 74 can include a handle 76 that can allow the button lever to be moved. The button lever 74 can be hingedly attached to the control unit 60 and biased towards an upright position. The button lever 74 can include internal spring. Pressing down on the handle 76 can move the button lever 74 downwards. An outer edge of the button lever 74 can engage an edge of the slot 66 in the tray. This engagement can keep the control unit 60 locked in place in the tray. It can also be seen that the control unit 60 has a handle 78 on underside of the control unit. The handles 78 and 76 can be used in conjunction to secure the control unit 60 while installing or removing the control unit 60 from the tray 10.

Figure 14:
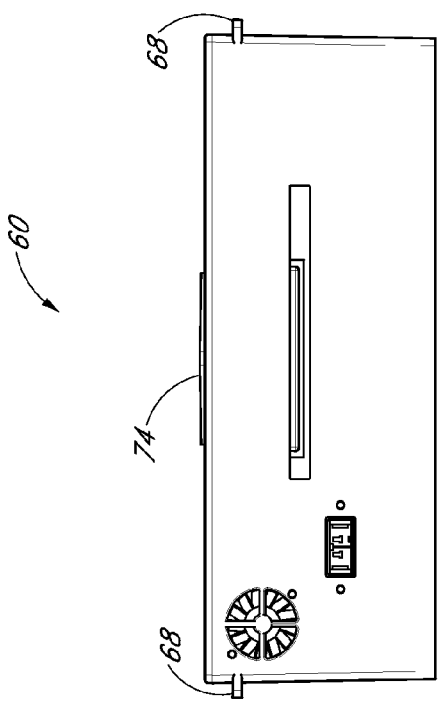

The control unit 60 can be provided with electrical connections (FIG. 14). The tray can also have corresponding electrical connections. This can allow the control unit to automatically engage the electrical connections of the tray when the control unit is inserted into the slot and engaged with the tray. The control unit 60 may be entirely self-contained or may require additional plug-ins such as outside power sources and other electrical or network-type connections.

In the case where the control unit 60 is connected to the tray 10 after the tray/pack is opened, it may not be necessary for the control unit 60 to be sterile. This is because the slot 66 in the tray is on a lower portion of the tray 10 which generally would not be in the sterile field or may be covered by a sterile drape.

The control unit 60 can have a processor (e.g., a microprocessor, ASIC, and/or circuitry and drive mechanism) and power configured to control and provide power to various instrumentations that require power and control on or attached to the tray 10. For example, the control unit 60 may be configured to power and control the vitreous cutter 26, the diathermy device 28, the illumination device 30, the motors 58 and/or the pumps 56. The control unit 60 may be equipped for wired or wireless communication. For example, the control unit 60 may communicate with the illumination device 30 for receiving current operating parameters, such as, for example, a current illumination level. In this manner, all the necessary logic, circuitry, and power can reside within the tray 10 itself and/or instruments in communication with the tray without having to resort to a separate control console. The control unit 60 preferably includes batteries and is rechargeable.

Figure 17:
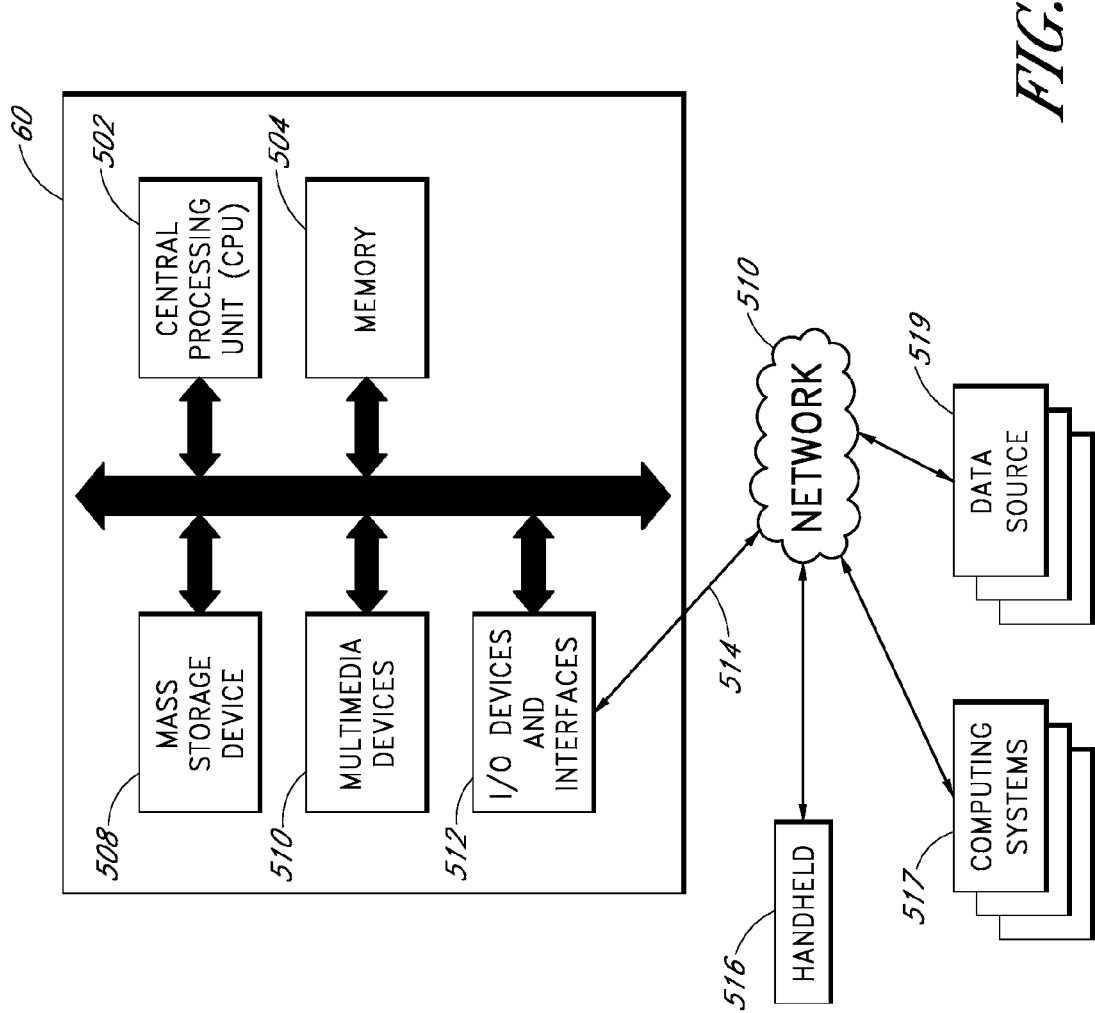
FIG. 17 is a block diagram of the components of a control unit.

Looking to FIG. 17, there is illustrated one embodiment of a control unit 60 that can be used with the tray 10. FIG. 17 illustrates a block diagram of a control unit 60 that is in communication with one or more handheld instruments 516 and/or computing systems 517 and/or data sources 519 via one or more networks 510. The control unit 60 may be used to implement one or more of the systems and methods described herein. In addition, in one embodiment, the control unit 60 may be configured to process status data and/or information from surgical devices. While FIG. 17 illustrates one embodiment of a control unit 60, it is recognized that the functionality provided for in the components and modules of control unit 60 may be combined into fewer components and modules or further separated into additional components and modules.

In one embodiment, the control unit 60 comprises a central processing unit ("CPU") 502, which may comprise a microprocessor. The control unit 60 further comprises a memory 504, such as random access memory ("RAM") for temporary storage of information and/or a read only memory ("ROM") for permanent storage of information, and a mass storage device 508, such as a hard drive, diskette, or optical media storage device.

The control unit 60 can comprise one or more commonly available input/output (I/O) devices and interfaces 512, such as a keyboard, mouse, touchpad, and printer. In one embodiment, the I/O devices and interfaces 512 comprise one or more display devices or touch screen display devices, such as a monitor, that allows the visual presentation of data to a user. The I/O devices and interfaces 512 can also provide a communications interface to various external devices. The control unit 60 may also comprise one or more multimedia devices 510, such as speakers, video cards, graphics accelerators, and microphones, for example. It will be understood that in some embodiments, the components discussed with regard to the control unit 60 can be physically located in the control unit 60, in the tray 10, or in another location.

In the embodiment of FIG. 17, the control unit 60 is coupled to a network 510, such as a LAN, WAN, or the Internet, for example, via a wired, wireless, or combination of wired and wireless, communication link 514. The network 510 communicates with various computing devices and/or other electronic devices via wired or wireless communication links. In the exemplary embodiment of FIG. 17, the network 510 is communicating with one or more handheld instruments 516, computing systems 517, and/or data sources 519. The control unit 60 may also include one or more pumps 56. Alternatively, the one or more pumps 56 can be part of a separate module or unit that can be connected to the tray. In this way, the one or more pumps can also be reusable which can reduce the cost of the tray 10.

Figure 19:
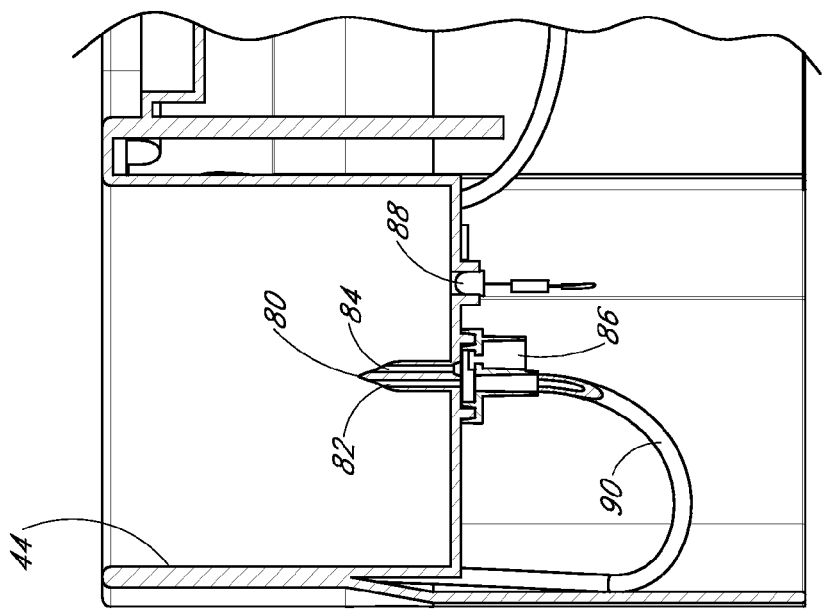
FIG. 19 is a cross-section taken along line 19-19 of FIG. 18.
Figure 18:
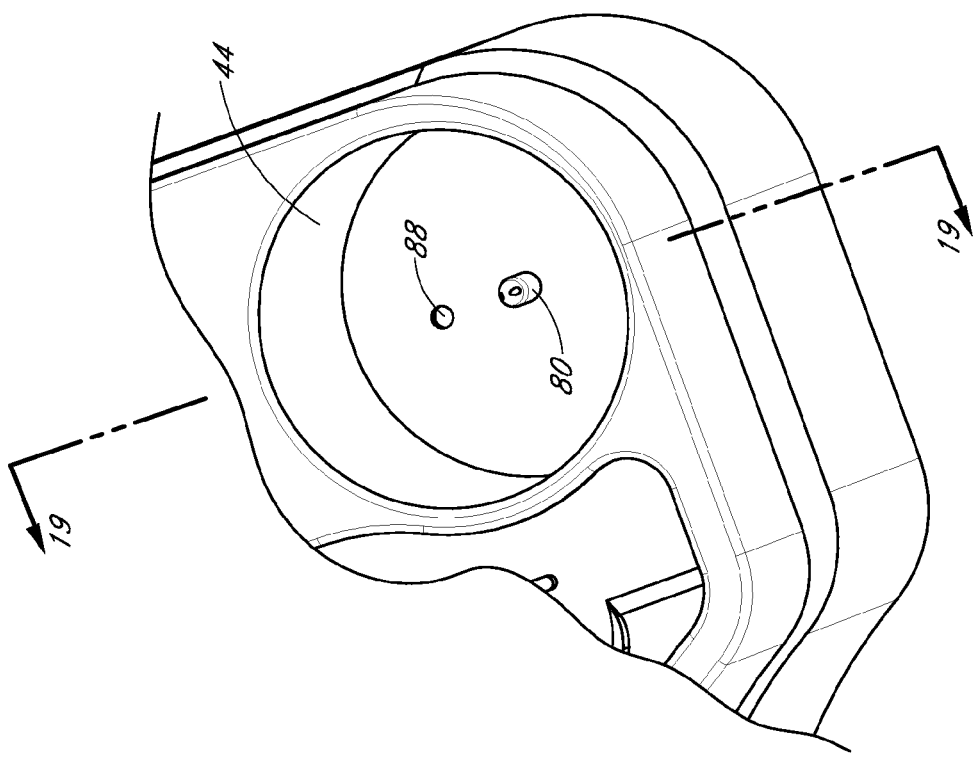
FIG. 18 is a section of the tray showing the fluid reservoir receiver.

Moving now to FIGS. 18 and 19, a detail of the tray 10 is shown. In particular, a fluid reservoir receiver or receptacle 44 is shown. The fluid reservoir receiver 44 can receive a reservoir or container of fluid, such as a bottle of balanced-salt solution (BSS). The fluid reservoir receiver 44 can be used to receive the fluid and then the fluid can be used by other components of the tray 10. For example, the fluid can be used by an infusion device and can be connected to the infusion pump 56 to pump the fluid to the infusion device and into the eye.

The fluid reservoir receiver 44 can be shaped like a bowl or a container. The fluid reservoir receiver 44 can be contoured to accommodate the shape of the desired fluid container. Preferably, the fluid reservoir receiver 44 can hold at least some fluid, if the fluid were to leak or be spilled from the container. As shown, the fluid reservoir receiver 44 has a substantially cylindrical wall and a planer bottom surface, though other cross-sectional shapes could be used, such as square, rectangular, polygon, etc.

The fluid reservoir receiver 44 can include a spike 80 or other device to gain access to the fluid within the bottle or container. As shown, the spike 80 is a vented spike having a fluid channel 82 and an air channel 84. Fluid can flow from the bottle or container through fluid channel 82 which passes into the tubing 90 connected with the spike 80. The tubing 90 can be connected to an infusion pump and/or an infusion instrument. The spike 80 can also include an air vent such as air channel 84. A filter 86, such as a hydrophobic air filter, can be used to allow air to flow into the spike while preventing fluid from exiting the spike through the air channel 84 and through the filter 86. In this way, the vented spike 80 allows for fluid to be removed from the container or bottle while at the same time allowing air to be introduced into the bottle. This reduces any pressure differential between the interior of the bottle and the atmosphere. This also allows the fluid to continuously exit the bottle as desired without becoming plugged or forced out because of the pressure differentials. Or alternatively, the air channel 84 may be connected to an infusion pump to pressurize the bottle or container so as to force fluid through tubing 90 as desired.

The fluid reservoir receiver 44 can also include a light 88. As many procedures in the eye are performed in the dark, a light 88 in the fluid reservoir receiver 44 can beneficially inform the surgeon as to the fluid level of the container or bottle of BSS fluid. The light 88 can be within, around, or outside of the fluid reservoir receiver 44. The light 88 is preferably located in the bottom surface of the fluid reservoir receiver 44, but can be positioned in other locations as well.

As illustrated in FIGS. 18 and 19, the light 88 is positioned next to the spike 80. The light 88 can be positioned in a radially middle location between the center of the fluid reservoir receiver 44 where the spike is located and the side wall. This allows the light 88 to be positioned next to a thin wall portion of the fluid bottle that is connected to the spike 80 within the fluid reservoir receiver 44. It will be understood that generally a conventional BSS bottle will have a thin wall portion between the neck and shoulder of the bottle. This will allow for increased light transmission through the bottle.

The light 88 can be received to form a fluid tight seal in the bottom of the fluid reservoir receiver 44. This way, if fluid leaks from the bottle it will be less likely to leak out of the tray 10 or the fluid reservoir receiver 44.

With the light 88 positioned in the bottom surface of the fluid reservoir receiver 44, the rays of light from the light 88 pass through bottle or container and through the fluid. The light 88 can highlight the fluid meniscus showing the level of fluid within the bottle. The meniscus is the curved upper surface of a column of liquid, the curvature of which is caused by surface tension between the fluid and the wall of the bottle or container. The light 88 is preferably an LED and is preferably a darker color so as to not distract from the surgical procedure. Example colors include blue, amber, purple, green, etc. Other types of lights, such as incandescent, florescent, and halogen, can also be used.

The illustrated configuration also beneficially prevents the light from shining directly into the surgeon's eyes or from otherwise becoming a distraction during the surgical procedure. Other systems can also be used to highlight the fluid level in the dark while not shining the light directly into the surgeon's eyes or otherwise being a distraction during the surgical procedure.

In many instances, a sterile user, such as a surgeon, may require the assistance of a non-sterile user without compromising the sterile field. For example, the surgeon may need the assistance of a non-sterile user to place or replace a sterile BSS bottle or other fluid, medication, injectable medication, intravenous solution or other container within the sterile field, such as on the tray 10, without compromising the sterile field.

Figure 20:
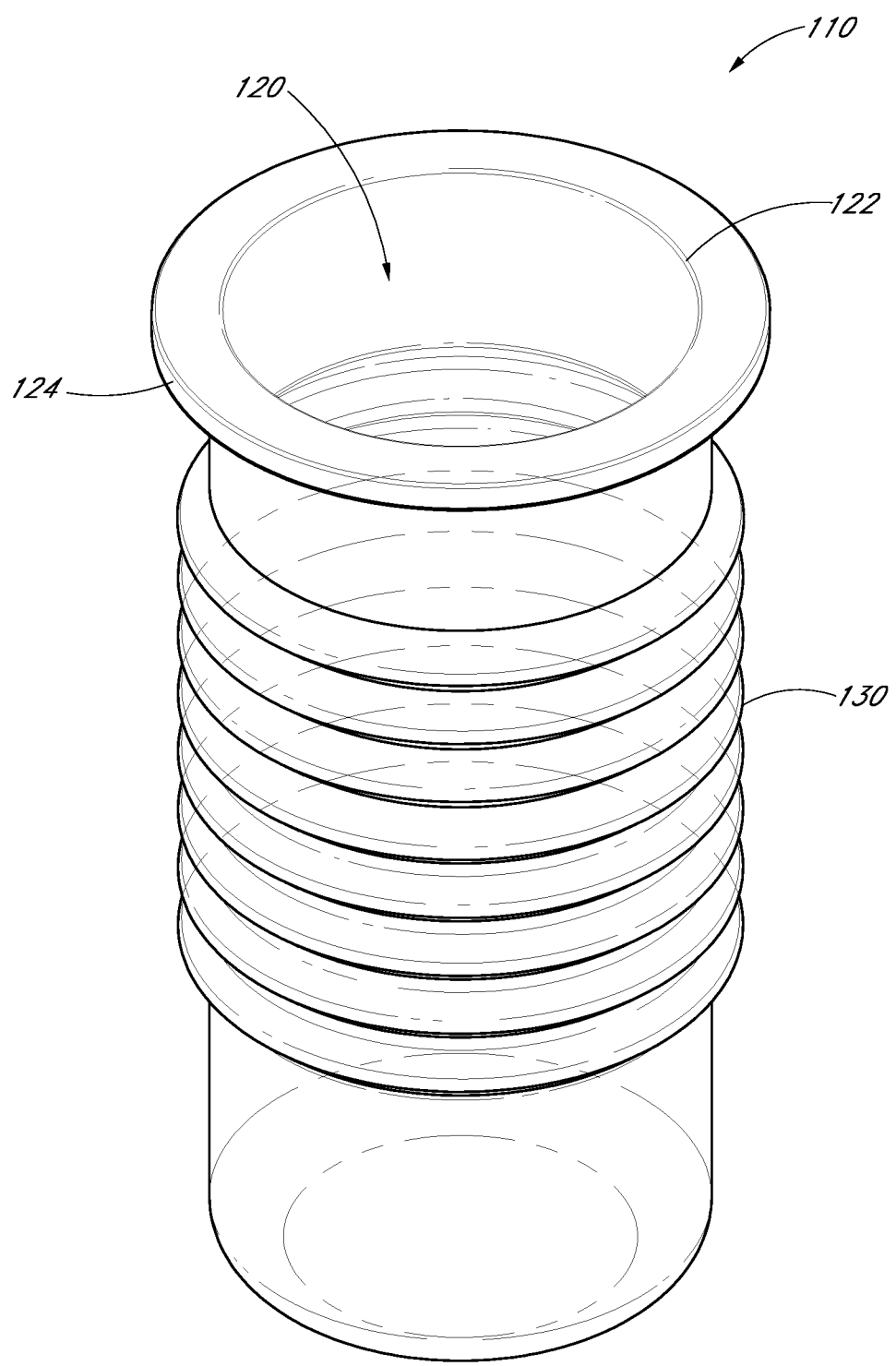
FIG. 20 shows a container.

FIG. 20 illustrates a device 110 that can be used to place a sterile item, such as a bottle within a sterile field without comprising the sterile field. The device 110 can also be used for other purposes.

The device 110 can be a container configured to hold a bottle, instruments, medication, tools, etc. The container 110 can have an internal chamber 120 with at least one opening 122. The internal chamber 120 and opening 122 can be used to hold or store other items. In some embodiments, the container 110 can further include a lip 124.

Figure 21:
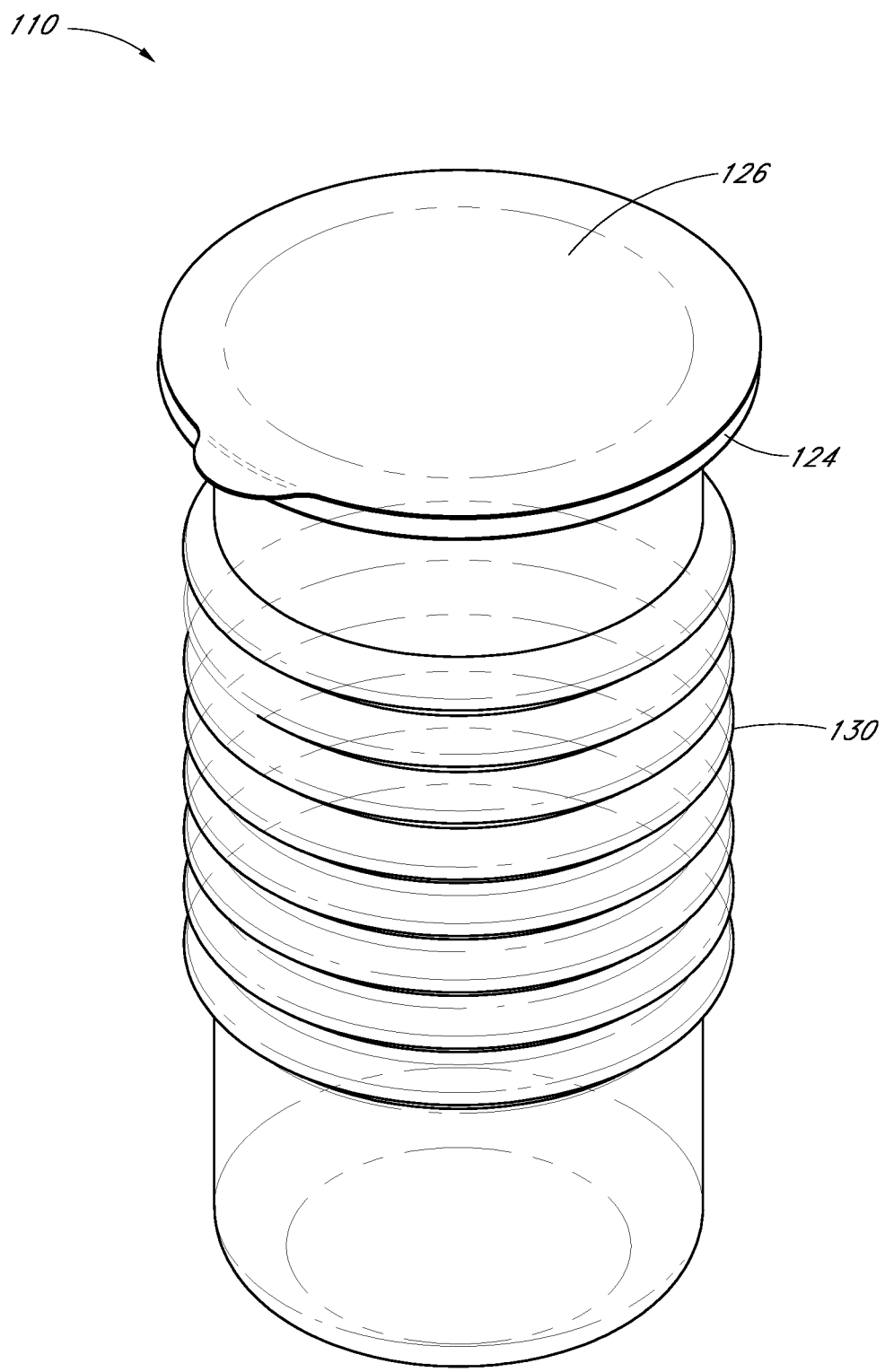
FIG. 21 shows a container with lid.

Turning now to FIG. 21, it can be seen that some embodiments a lid 126 can cover the top of the container 110. The lid 126 can seal the opening 122 and internal chamber 120. For example, the container and/or the internal chamber 120 can be sterilized and a sterile lid 126 can then be attached to the container 110. Alternatively, the lid 26 can be a TYVEK® lid that can allow the container 110, the internal chamber 120, and anything within the internal chamber 120 to be sterilized together. This can maintain the internal chamber 120 in a sterilized configuration, at least until the lid 126 is removed or the sealed internal chamber 120 is otherwise breached.

The lid 126 can attach to the lip 124. As shown, the lid 126 is a TYVEK® lid or other similar material. The lid 126 can be any type of lid that can maintain the internal chamber 120 in a sterile condition.

In some embodiments, an item that has been previously sterilized can be placed within the internal chamber 120. The lid can then be placed on the container 110. Alternatively, or in addition, an item and the internal chamber 120 can be jointly sterilized prior to attaching the lid 126, or after the lid 126 has been attached.

In some embodiments, the container 110 and an item can be sterilized (jointly or separately), the item can be placed within the container, and the container is then placed within a further container such that a lid 126 is unnecessary. The further container could be packaging or a medical kit, for example. The container 110 and the item could also be sterilized while within the further container.

Figure 22:
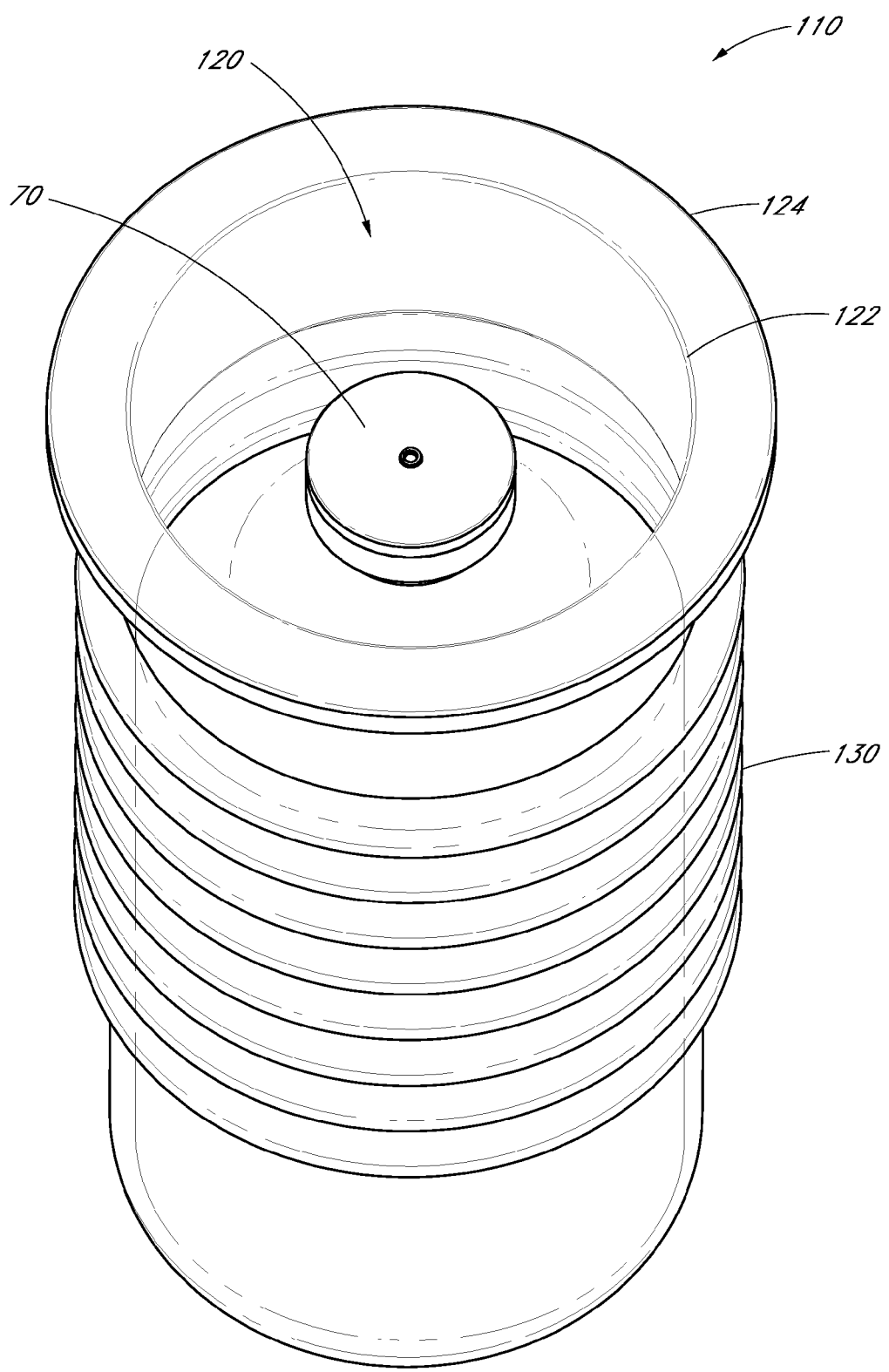
FIG. 22 shows a bottle within a container.

FIG. 22 illustrates an embodiment of the container 110 with a bottle 70 within the internal chamber 120 of the container 110. The bottle 70 can contain any of a number of different substances including IV fluid, saline, and medication. In a preferred embodiment, the bottle 70 is a sterile bottle containing balanced-salt solution (BSS).

In some embodiments, all or part of the container 110 can be flexible and/or malleable. This flexibility and malleability can allow a user to exert forces on the container that can be imparted to item(s) within the container 110. For example, the container 110 can have a compressible section 130. In some embodiments, the compressible section 130 comprises an accordion shaped feature that can allow the container to be compressed and/or decrease in size.

Figure 23A:
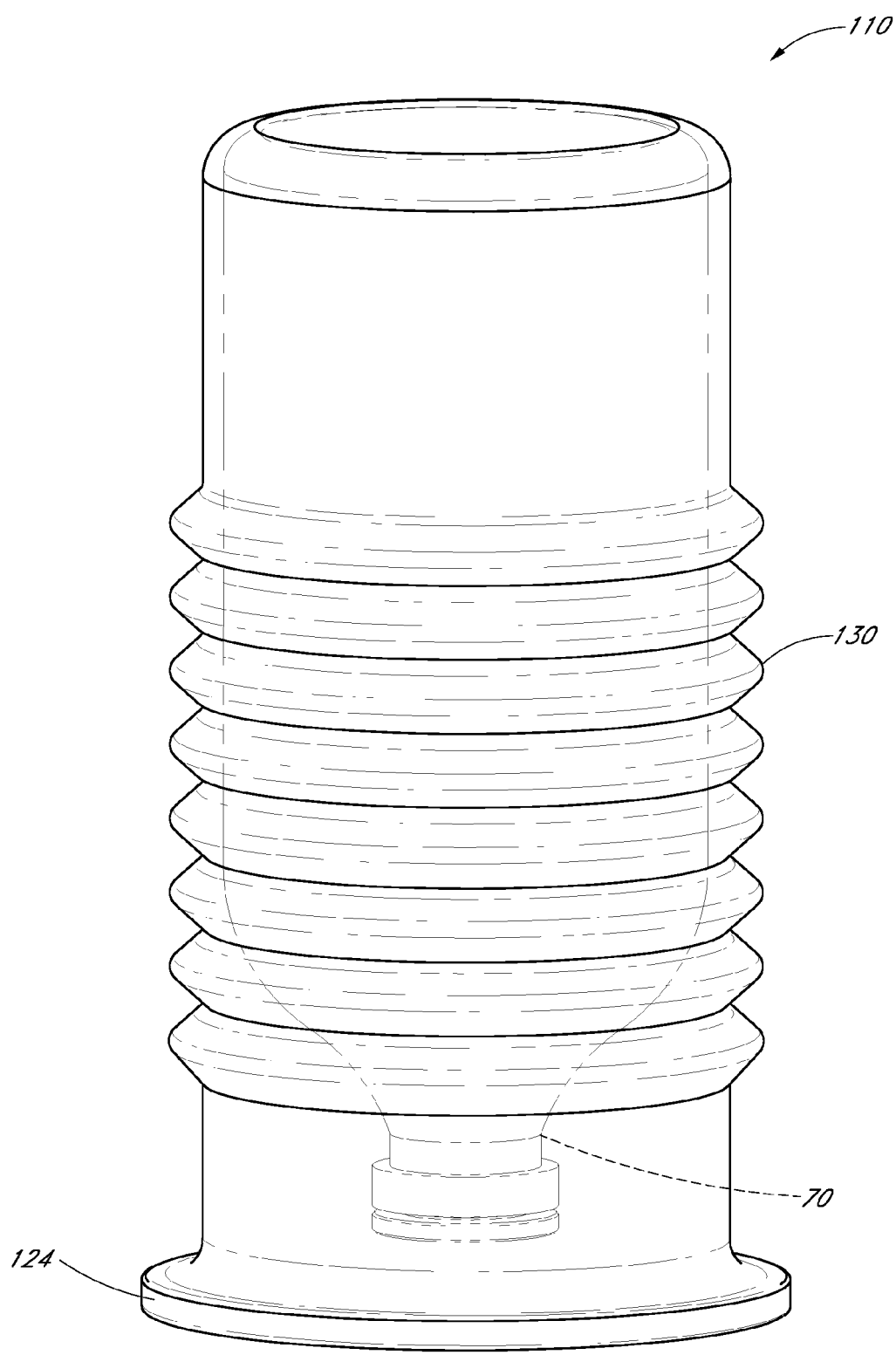
FIG. 23A shows a bottle within a container.
Figure 23B:
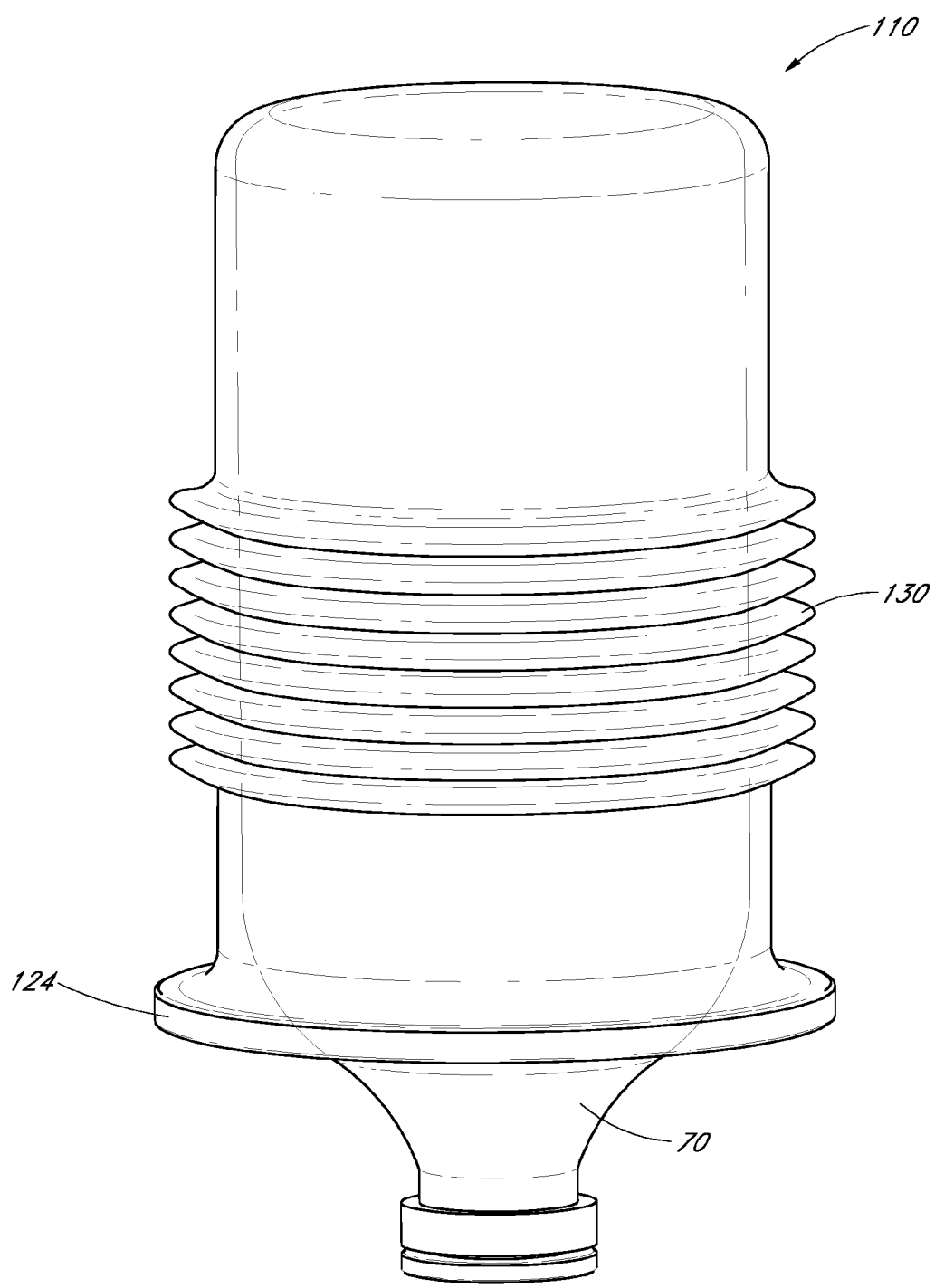
FIG. 23B shows the bottle within a container with the container in a compressed state.

FIGS. 23A-B illustrate one embodiment of a container 110 where the compressible section 130 is moved to the compressed state, decreasing the size of the container 110. In comparison to FIG. 23A, where the bottle 70 was completely within the container 110, in FIG. 23B the bottle 70 now extends past the opening 122 and lip 124 of the container. The compressible section 130 can allow a user to have increased control over the movement of an item within the container. The compressible section 130 can be used to, for example, force an item out of the container 110. The compressible section 130 can also allow the force to be applied to the item as it leaves the container 110, as will be further explained below.

As one example, the container 110 can be used to advance the bottle 70 onto a spike in the fluid reservoir receiver 44 of the tray 10. The compressible section 130 can allow the doctor or nurse to apply the necessary pressure on the bottle, so that the spike can pierce the septum or lid of the bottle. This can provide access to the BSS fluid within the bottle 70 to the various instruments on the tray. For example, the infusion pump 56 can be used to pump BSS fluid from the bottle 70 to the vitreous cutter 26. The container 110 can advantageously allow a non-sterile user, such as a nurse to load the BSS fluid onto the sterile tray 10 without compromising the sterile field.

Some example uses of the container 110 will now be described.

As has been previously mentioned, a sterile field can be established for a medical or surgical procedure that may involve a tray or pack 10. In surgery, a sterile pack can be shipped from a manufacturer to a surgery center. An example of which is ophthalmic surgery (vitreoretinal or cataract surgery, in particular). These packs can contain several items that are typically used in surgery and include one-time use surgical instruments, fluid cassettes, tubing sets, drapes, needles, and other devices. The particular content of a pack depends on the type of surgery and perhaps the individual preference of the surgeon or surgical center.

When preparing for surgery, a sterile drape can be placed over a tray. The contents of the sterile pack and perhaps additional sterile instruments and materials are spread-out over the tray so that the materials and instruments necessary for the surgery are readily available to a nurse or surgeon. A sterile pack can also be provided where many of the instruments and tubing sets are organized and placed in mating recesses of the pack so that the pack can act as a tray for at least some of the instruments in surgery. In such an example, a sterile drape may not be needed.

Often times, after the pack is opened, the components within the pack are retrieved and transferred to a conventional tray, as is known in the art, or back table in an operating room such that a surgeon can retrieve and, if he/she desires, place back any of the components during an operation. Often times, a scrub nurse or surgical assistant performs this transfer.

The components within a pack or for a surgical procedure can vary substantially. For example, surgical components of a surgical pack for an ophthalmic procedure can include: a biological tissue cutter; a tissue illuminator; an aspiration/ infusion cassette; a disposable speculum/drape combination; a self stabilizing lens ring with the lens pre-mounted; a gas exchange syringe; Q-tips; a sterile container containing balanced salt solution (BSS); an infusion line; trocars with cannulas pre-mounted; and goniosol.

In some procedures, the aspiration/infusion cassette is mounted directly into the tray. This eliminates the need for separate setup of the aspiration/infusion cassette. An aspiration line connects the biological tissue cutter to the aspiration chamber of the cassette for removing tissue cut or dislodged by the cutter during surgery. The infusion line connects the infusion chamber of the cassette and allows infusion of fluids such as, for example, the balanced salt solution, to replace the aspirated materials.

Referring now to FIGS. 24-27, the tray 10 can accept a sterile container 70 of balanced salt solution directly into the tray. This can allow the container 70 to be connected to a pump that can allow the infusion of fluids into the eye, for example. The container 110 can be used to facilitate the installation, placement and/or replacement of the container 70 into the fluid reservoir receiver 44 of the tray 10.

The following steps may be taken during a surgical procedure to mount the container 70 onto the tray 10. The below steps can be performed by a non-sterile user without comprising the sterile field.

1) The lid 126 can be removed from the container 110, and/or the container 110 can be removed from packaging. The container 110 can contain a sterile bottle 70 of IV fluid, such as BSS.

2) The container 110 can be turned upside down to insert the bottle 70 into the fluid reservoir receiver 44 of the tray 10 as shown in FIG. 24. The bottle 70 can be held in place within the container 110 by grip of the user, or by a slight friction fit between the bottle and the container. The bottle 70 may be loose inside the container 110 so as to be able to slide out without additional force, or with minimal force.

3) The container 110 can be placed over the fluid reservoir receiver 44 of the tray 10 with the top down so that the opening 122 of the container is adjacent the top opening of the fluid reservoir receiver 44 (FIG. 25). The bottle 70 can be allowed out of the container into the fluid reservoir receiver 44.

4) With the bottle placed within or over the fluid reservoir receiver 44 (FIG. 25), a downward force can be applied to the bottom of the container 110 (FIG. 26). This force can be a way to ensure that the bottle is securely attached to the tray. This movement may also serve to provide other functions such as puncturing an end of the bottle with the spike 80 (FIGS. 18-19) within the tray or locking the bottle in place.

This downward force can collapse the collapsible section 130. This is because the lip 124 of the container is positioned on the tray 10 so the force can be sufficient to cause the collapsible section to decrease in size. The force can cause the compressible section 130 to compress, such as in an accordion fashion.

The force can also push the bottle 70 downward. This can cause the bottle to leave the container. When the fluid reservoir receiver 44 includes a spike 80, the force can also press the bottle onto the spike. The spike can advance through the bottle, such as through a septum or lid of the bottle. The bottle can then be fluidly connected to the tray so that the pump 56 can draw fluid from the container to be used at one or more parts of the tray. For example the fluid can be provided to an instrument, such as a vitreous cutter 26 and to a priming fluid reservoir 20.

Figure 27:
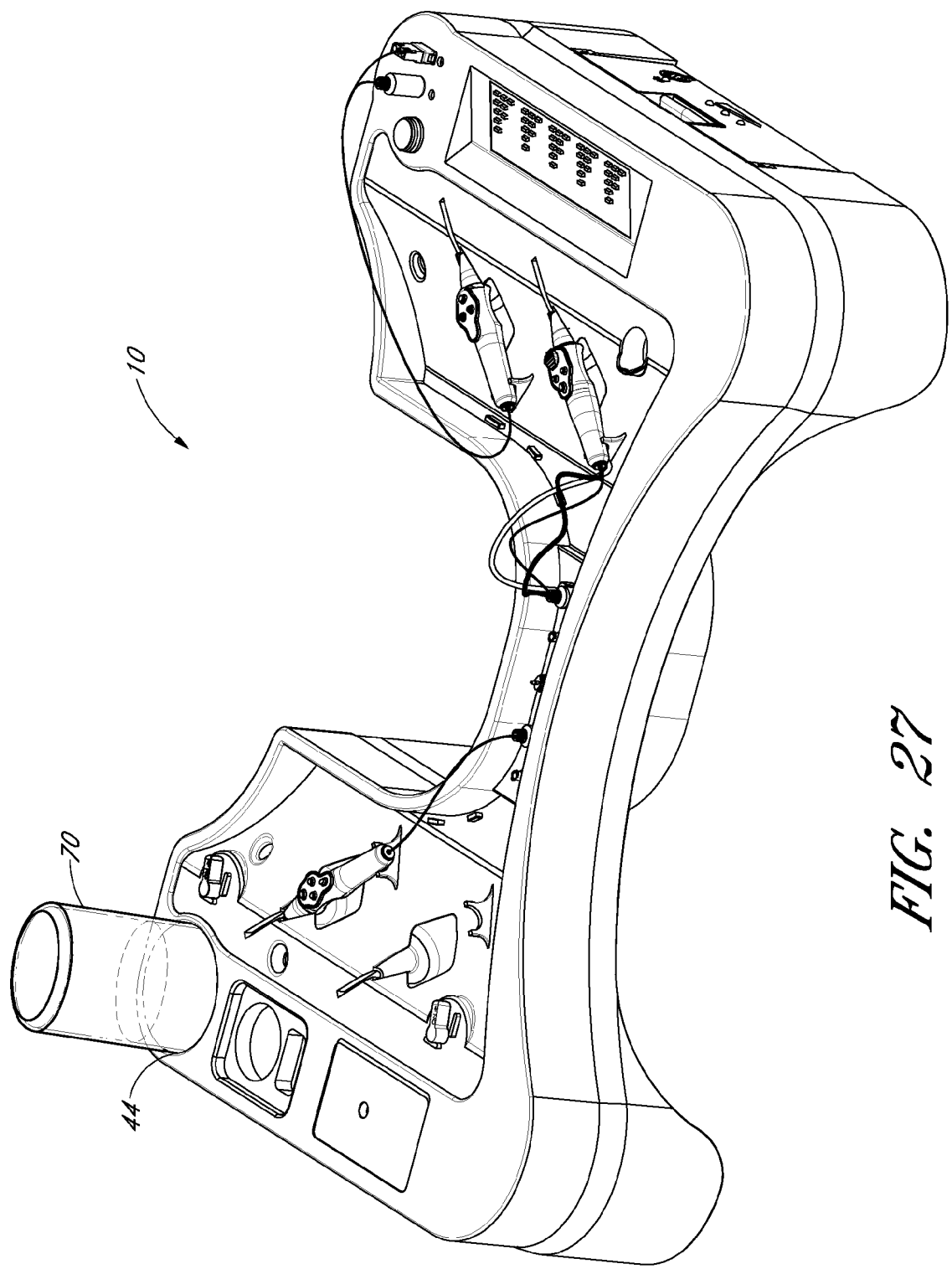

5) Once the bottle 70 is securely in place, the container 110 can be removed and discarded. The BSS container is then contained in the fluid reservoir receiver 44 of the tray 10 as shown in FIG. 27.

Preferably, the above method steps are performed by a non-sterile user. Because the container 110 is removed and discarded, and the user does not contact the bottle 70 and the sterile field is generally not compromised. The outside surface of the bottle 70 is preferably sterile and the sterile container 110 which may have been touched by the non-sterile user has been removed. The container 110 allows the non-sterile user to attach the bottle 70 to the tray without having to touch any part of the tray or the bottle.

Should the surgeon or sterile user require an additional or new bottle 70, such as of BSS solution, the sterile user can assist without compromising the sterile field. The sterile user can remove and discard the empty sterile bottle 70 from the tray 10 and the above steps can then be repeated to install a new bottle 70.

A person of skill in the art should recognize that one or more of the steps may vary depending on the type of surgery performed. For example, all of the above steps can be performed by a sterile user such as a surgeon.

As another example, the container 110 can also be used to cover a device having a non-sterile exterior. For example, the container 110 can be sterilized and a bottle having a non-sterilize exterior or other item can be placed within the container 110. The container 110 can provide a protected, sterile covering for the bottle so as to not compromise the sterile field.

As an example for a method of use, a bottle having a non-sterile exterior, such as a bottle containing BSS can be placed within the container 110. The container 110 can then be used as described above, to secure the bottle 70 to the tray 10. The container 110 can remain covering the bottle 70, as in FIG. 26. This can provide for a sterile surface within the sterile field, while still allowing for the use of a bottle or item having a non-sterile exterior.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A surgical apparatus for use by a surgeon during a surgical procedure comprising:
   a sealed sterilized surgical pack comprising:
      a plurality of surgical instruments; and
      a surgical tray being substantially shaped to fit around a body part of a patient and comprising:
         a top surface configured to be part of a sterile field of a surgical procedure;
         a plurality of receiving structures located on the top surface, each of the plurality of surgical instruments removably positioned in a corresponding one of the receiving structures;
         at least one electrical connector, at least one of the plurality of surgical instruments being connected to the at least one electrical connector;
         at least one fluid connector, at least one of the plurality of surgical instruments being connected to the at least one fluid connector; and
         a side or bottom surface configured to be outside of the sterile field, the side or bottom surface comprising a control unit receiver, the control unit receiver being electrically coupled to the at least one electrical connector; and
   a control unit configured to be received into the control unit receiver after the surgical pack has been opened, the control unit configured to power and control operation of at least one of the plurality of surgical instruments; wherein the tray further comprises a receiver for receiving a container of fluid, wherein the receiver comprises a spike and a light positioned within the receiver for shining light through the container of fluid to indicate a fluid level to the surgeon.

2. The surgical apparatus of claim 1, wherein the control unit receiver is positioned below the sterile field.

3. The surgical apparatus of claim 1, wherein the control unit is non-sterile.

4. The surgical apparatus of claim 3, wherein the control unit further comprises rechargeable batteries.

5. The surgical apparatus of claim 1, further comprising at least one pump connected to the at least one fluid connector, the control unit receiver being electrically coupled to the pump.

6. The surgical apparatus of claim 1, wherein the plurality of surgical instruments comprises a biological tissue cutter, and a tissue illuminator.

7. The surgical apparatus of claim 1, wherein the tray is configured to sit on a surgical stand to a side of or on top of the patient.

8. The surgical apparatus of claim 1, wherein the surgical tray being substantially shaped to fit around the body part of the patient comprises the surgical tray being substantially U-shaped.

9. The surgical apparatus of claim 8, wherein the surgical tray further comprises a mating recess on a bottom side of the tray, the mating recess configured to receive a portion of a tray support on a surgical table or chair such that the tray can be attached to the tray support.

* * * * *